US011480634B2

(12) United States Patent
Lim et al.

(10) Patent No.: US 11,480,634 B2
(45) Date of Patent: Oct. 25, 2022

(54) APPARATUS AND METHOD FOR NANO MAGNETIC PARTICLE IMAGING

(71) Applicant: Electronics and Telecommunications Research Institute, Daejeon (KR)

(72) Inventors: Eul-Gyoon Lim, Daejeon (KR); Jin-Sun Kim, Daejeon (KR); Chang-Beom Kim, Daejeon (KR); Jae-Chan Jong, Daejeon (KR); Seung-Min Choi, Daejeon (KR); Hyo-Bong Hong, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 17/318,753

(22) Filed: May 12, 2021

(65) Prior Publication Data

US 2021/0405134 A1 Dec. 30, 2021

(30) Foreign Application Priority Data

Jun. 25, 2020 (KR) .................. 10-2020-0078008

(51) Int. Cl.
*G01R 33/12* (2006.01)
*A61B 5/0515* (2021.01)
*G01B 21/22* (2006.01)

(52) U.S. Cl.
CPC ......... *G01R 33/1276* (2013.01); *G01B 21/22* (2013.01); *A61B 5/0515* (2013.01)

(58) Field of Classification Search
CPC .............. G01R 33/1276; G01R 33/028; G01R 33/038; G01R 33/20; G01B 21/22; A61B 5/0515

See application file for complete search history.

(56) References Cited

U.S. PATENT DOCUMENTS 10,267,867 B2   4/2019  Choi et al.
10,948,556 B2   3/2021  Hong et al.
(Continued)

FOREIGN PATENT DOCUMENTS

KR   1020190063866 A   6/2019
KR   1020210027049 A   3/2021
(Continued)

OTHER PUBLICATIONS

P. W. Goodwill, J. J. Konkle, B. Zheng, E. U. Saritas and S. M. Conolly, "Projection X-Space Magnetic Particle Imaging," in IEEE Transactions on Medical Imaging, vol. 31, No. 5, pp. 1076-1085, May 2012 (Year: 2012).*
(Continued)

*Primary Examiner* — Daniel R Miller
(74) *Attorney, Agent, or Firm* — William Park & Associates Ltd.

(57) ABSTRACT

Disclosed herein is a nano-magnetic-particle-imaging apparatus, including a measurement head including excitation and detection coils and accommodating a sample bed for a sample including nano magnetic particles; a gradient magnetic field generation unit for generating a magnetic field having a strength equal to or greater than that of the saturation magnetic field of the nano magnetic particles in a spacing area between identical magnetic poles facing each other and forming a field-free region in a portion thereof; a first driving unit for linearly moving the sample bed; a second driving unit for rotating the gradient magnetic field generation unit in a plane; a third driving unit for linearly reciprocating the gradient magnetic field generation unit; and a control unit for applying a signal to the excitation coil, controlling the driving units, and imaging 3D distribution of the nano magnetic particles based on a detection signal output from the detection coil.

20 Claims, 21 Drawing Sheets

(56) References Cited

U.S. PATENT DOCUMENTS

| | | | |
|---|---|---|---|
| 2014/0159712 A1* | 6/2014 | Graziani | A61B 5/0515 |
| | | | 324/232 |
| 2017/0067971 A1 | 3/2017 | Choi et al. | |
| 2018/0017641 A1 | 1/2018 | Goodwill | |
| 2019/0079149 A1 | 3/2019 | Conolly et al. | |
| 2019/0255174 A1 | 8/2019 | Creighton | |
| 2021/0059557 A1 | 3/2021 | Jong et al. | |

FOREIGN PATENT DOCUMENTS

| | | | |
|---|---|---|---|
| KR | 1020210043422 A | 4/2021 | |
| WO | WO-2015078527 A1 * | 6/2015 | A61B 5/0515 |

OTHER PUBLICATIONS

Klass Bente et al., Electronic Field Free Line Rotation and Relaxation Deconvolution in Magnetic Particle Imaging, IEEE Transactions on Medical Imaging, vol. 34, Issue: 2, pp. 644-651, Feb. 2015.

Patrick W. Goodwill et al., Projection X-Space Magnetic Particle Imaging, IEEE Transactions on Medical Imaging, vol. 31, No. 5, pp. 1076-1085, May 2012.

* cited by examiner

APPARATUS AND METHOD FOR NANO MAGNETIC PARTICLE IMAGING

CROSS REFERENCE TO RELATED APPLICATION

This application claims the benefit of Korean Patent Application No. 10-2020-0078008, filed Jun. 25, 2020, which is hereby incorporated by reference in its entirety into this application.

BACKGROUND OF THE INVENTION

1. Technical Field

The disclosed embodiment relates generally to technology for imaging a specific object included in a sample, and more particularly to technology for imaging the spatial distribution of Nano Magnetic Particle (NMP) materials.

2. Description of the Related Art

'Magnetic Particle Imaging (MPI)' is the field of diagnostic medical device technology through which a body part affected by a disease can be determined based on the distribution of magnetic nanoparticles in a living body using a phenomenon in which, when magnetic nanoparticles, such as iron oxide, are coated with antibodies and injected into a living body, antigen-antibody reaction causes the magnetic nanoparticles to be temporarily attached to the region where a specific disease occurs.

Magnetic nanoparticles usually have no magnetism. However, when placed in a magnetic field, magnetic nanoparticles become magnetized in proportion to the strength of the magnetic field, and when the strength exceeds the strength of a unique saturation magnetic field of the magnetic nanoparticles, no more magnetization occurs. Because magnetic nanoparticles are characterized by low magnetic hysteresis, they generate a linear signal in an AC magnetic field, the strength of which is equal to less than the strength of the saturation magnetic field thereof, generate a nonlinear signal in an AC magnetic field, the strength of which fluctuates above and below that of the saturation magnetic field, and generate a weak signal or no signal in an AC magnetic field, the strength of which always exceeds that of the saturation magnetic field.

A paper, titled "Electronic Field Free Line Rotation and Relaxation Deconvolution in Magnetic Particle Imaging" and written by Klaas Bente, suggests a method in which five pairs of electromagnet coils are installed so as to surround the entire space in which the biological sample to be measured is placed, a magnetic field gradient is formed such that a magnetic-field-free region takes the form of a field-free point or a field-free line (referred to as an FFL hereinbelow), and the value of current at that time is changed using a predetermined method to cause rotation and parallel translation of the gradient magnetic field, whereby a signal is generated only in magnetic nanoparticles within a specific space for a moment. This method requires a high amount of current because it is difficult to increase the number of turns of a coil due to the pancake shape thereof, and has a disadvantage in that heat is generated in an amount proportional to the square of the amount of current.

In another paper, titled "Projection x-space magnetic particle imaging", written by Goodwill P. W. and published on May 31, 2012, an FFL, generated using a pair of magnets, is moved linearly using a pair of coils, and a sample, rather than the FFL, is rotated. Also, in Patent Document 1 (U.S. Patent Application Publication No. US2018/0017641, published on Jan. 18, 2018), an FFL, generated using a pair of magnets, is moved linearly using a pair of coils, and the magnets are rotated using a mechanical means. However, these methods have a disadvantage in that it is difficult to increase the size of an electromagnetic coil, which is a means for parallel translation of an FFL, due to the problems of high amounts of input power and generated heat.

DOCUMENTS OF RELATED ART (Patent Document 1) U.S. Patent Application Publication No. 2018/0017641, published on Jan. 18, 2018.

SUMMARY OF THE INVENTION

An object of an embodiment is to solve problems in which a large amount of current is required for imaging the spatial distribution of Nano Magnetic Particle (NMP) materials and in which heat is generated in an amount proportional to the square of the amount of current.

Another object of an embodiment is to reduce the size of an apparatus for imaging the spatial distribution of Nano Magnetic Particle (NMP) materials.

An apparatus for imaging nano magnetic particles according to an embodiment may include a measurement head in which an excitation coil and a detection coil are installed and in which a sample bed, on which a sample including nano magnetic particles is placed, is accommodated; a gradient magnetic field generation unit for generating a magnetic field having a strength equal to or greater than a strength of a saturation magnetic field of the nano magnetic particles in a spacing area between identical magnetic poles facing each other and for forming a field-free region, in which there is a weak magnetic field or no magnetic field, in a portion of the spacing area; a first driving unit for linearly moving the sample bed in a direction in the spacing area; a second driving unit for rotating the gradient magnetic field generation unit in a plane perpendicular to the direction; a third driving unit for converting rotation into sinusoidal reciprocation, thereby causing the gradient magnetic field generation unit to linearly reciprocate in the plane; and a control unit for applying a signal to the excitation coil when the sample bed is located in the spacing area of the gradient magnetic field generation unit, controlling the first driving unit, the second driving unit, and the third driving unit so as to move the field-free region in the sample, and imaging 3D positional distribution of the nano magnetic particles included in the sample based on a detection signal output from the detection coil.

Here, the excitation coil may include a low-frequency coil and a high-frequency coil and may generate a mixed magnetic field by mixing a first magnetic field, generated in the low-frequency coil, with a second magnetic field, generated in the high-frequency coil.

Here, the identical magnetic poles facing each other may be formed using a pair of permanent magnets that generate a gradient magnetic field in a plane.

Here, the identical magnetic poles facing each other may be further formed using a pair of DC coils that generate a gradient magnetic field in another plane perpendicular to the plane.

Here, the second driving unit may include a support in which a through hole is formed; a rotation part formed in a cylindrical shape to be inserted into the through hole, the rotation part accommodating the gradient magnetic field generation unit by joining the same to an inner side thereof; and a first motor for rotating the rotation part in response to a control signal input from the control unit.

Here, the apparatus may further include a first detection unit for measuring a reference point or a rotation angle of the rotation part.

Here, the rotation part may further include a linear guide joined to the gradient magnetic field generation unit on the inner side thereof, the linear guide guiding the gradient magnetic field generation unit so as to linearly move in the plane, and the third driving unit may be a scotch yoke that is formed to be joined between the inner side of the rotation part and the gradient magnetic field generation unit, the scotch yoke causing the gradient magnetic field generation unit to linearly reciprocate along the linear guide by converting rotation into sinusoidal reciprocation.

Here, the scotch yoke may include a sliding yoke fixed to the gradient magnetic field generation unit and including a slot formed in a direction perpendicular to a transfer direction of the linear guide; a crank to which an eccentric pin engaging the slot is joined as an integral part thereof; and a second motor supplying torque to a center of the crank.

Here, a mass of the crank may be equivalent to a mass of the gradient magnetic field generation unit.

Here, the crank may be used as a flywheel having an increased moment of rotational inertia.

Here, the apparatus may further include a second detection unit for measuring a reference point or a rotation angle of a central axis of the crank.

Here, the control unit may generate a 2D image, which is 2D positional distribution of nano magnetic particles included in a cross section of the sample, based on the detection signal, and may generate a 3D image by synthesizing multiple 2D images corresponding to multiple cross sections that are parallel to each other.

Here, the control unit may perform control so as to repeat rotation of the gradient magnetic field generation unit by the second driving unit and linear reciprocation thereof by the third driving unit, and may generate a sinogram using a signal output from the detection signal according to movement of the field-free region and generate the 2D image by performing inverse radon transform on the generated sinogram.

Here, the control unit may control the second driving unit so to intermittently rotate the gradient magnetic field generation unit, and may delete data acquired during rotation from a sinogram generated as a result of intermittent rotation.

Here, the control unit may control the second driving unit to continuously rotate the gradient magnetic field generation unit, and may generate a sinogram through 2D interpolation of a detection signal acquired as a result of continuous rotation.

A method for imaging nano magnetic particles according to an embodiment may include applying a signal to an excitation coil installed in a measurement head in which a sample including nano magnetic particles is accommodated; and generating a magnetic field having a strength equal to or greater than a strength of a saturation magnetic field of the nano magnetic particles in a spacing area between identical magnetic poles facing each other, moving a field-free region, in which there is a weak magnetic field or no magnetic field and which is formed in a portion of the spacing area, in the sample, and imaging 3D positional distribution of the nano magnetic particles included in the sample based on a detection signal output from a detection coil of the measurement head. The field-free region is linearly moved in one direction, is rotated in a plane perpendicular to the one direction, or is caused to linearly reciprocate in the plane through conversion of rotation into sinusoidal reciprocation Here, imaging the 3D positional distribution of the nano magnetic particles may include generating a 2D image, which is 2D positional distribution of nano magnetic particles included in a cross section of the sample, based on the detection signal; and generating a 3D image by synthesizing multiple 2D images corresponding to multiple cross sections that are parallel to each other.

Here, generating the 2D image may include repeating rotation and linear reciprocation of the field-free region; generating a sinogram using a signal output from the detection signal according to movement of the field-free region; and generating the 2D image by performing inverse radon transform on the generated sinogram.

Here, generating the 2D image may be configured to intermittently rotate the field-free region and to delete data acquired during rotation from the sinogram generated as a result of intermittent rotation.

Here, generating the 2D image may be configured to continuously rotate the field-free region and to generate the sinogram through 2D interpolation of the detection signal acquired as a result of continuous rotation.

BRIEF DESCRIPTION OF THE DRAWINGS

The above and other objects, features and advantages of the present invention will be more clearly understood from the following detailed description, taken in conjunction with the accompanying drawings, in which.

DESCRIPTION OF THE PREFERRED EMBODIMENTS

Figure 1:
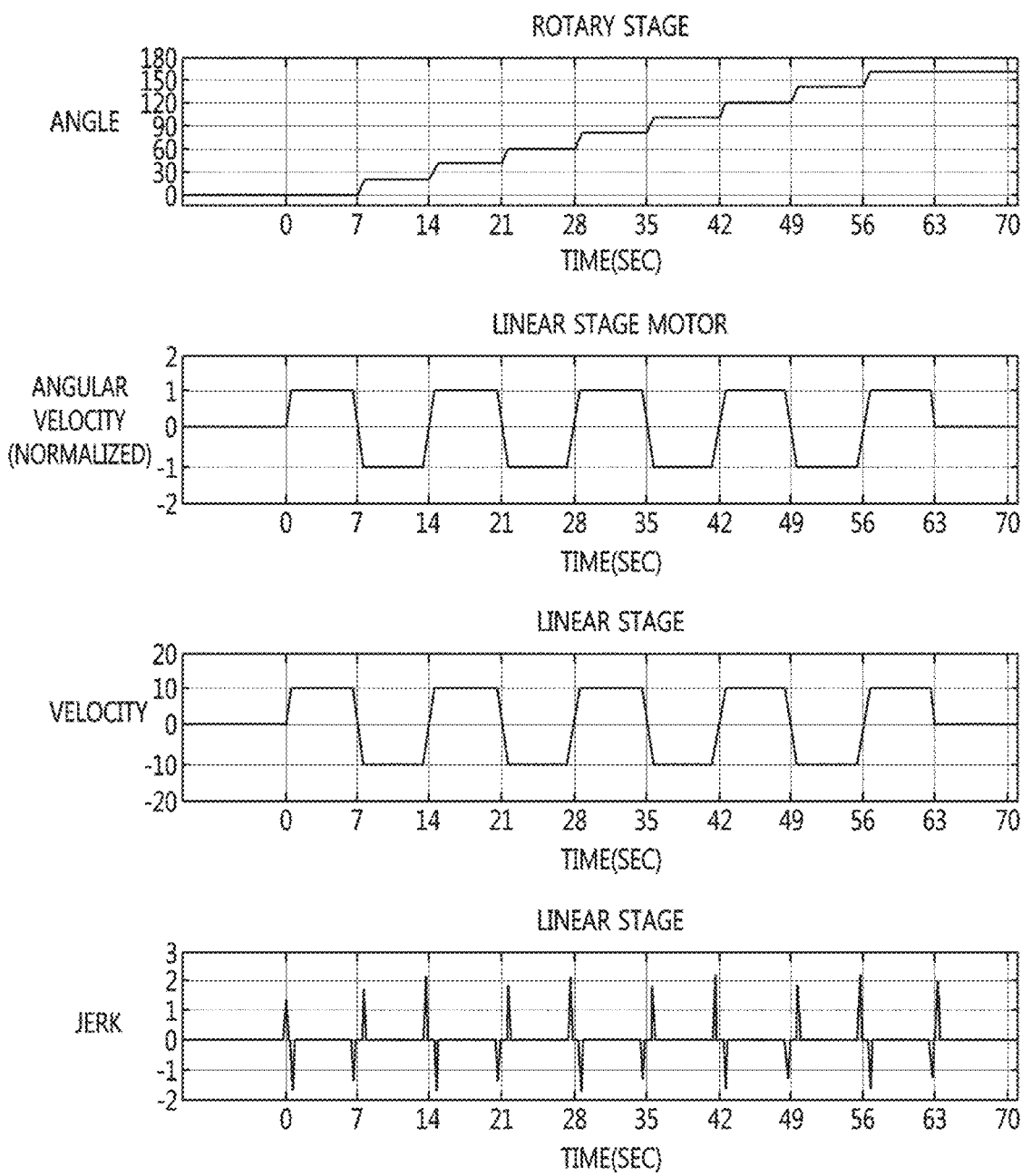
FIG. 1 is a view for explaining an operation for movement of a general field-free region.

The advantages and features of the present invention and methods of achieving the same will be apparent from the exemplary embodiments to be described below in more detail with reference to the accompanying drawings. However, it should be noted that the present invention is not limited to the following exemplary embodiments, and may be implemented in various forms. Accordingly, the exemplary embodiments are provided only to disclose the present invention and to let those skilled in the art know the category of the present invention, and the present invention is to be defined based only on the claims. The same reference numerals or the same reference designators denote the same elements throughout the specification.

It will be understood that, although the terms "first," "second," etc. may be used herein to describe various elements, these elements are not intended to be limited by these terms. These terms are only used to distinguish one element from another element. For example, a first element discussed below could be referred to as a second element without departing from the technical spirit of the present invention.

The terms used herein are for the purpose of describing particular embodiments only, and are not intended to limit the present invention. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

Unless differently defined, all terms used herein, including technical or scientific terms, have the same meanings as terms generally understood by those skilled in the art to which the present invention pertains. Terms identical to those defined in generally used dictionaries should be interpreted as having meanings identical to contextual meanings of the related art, and are not to be interpreted as having ideal or excessively formal meanings unless they are definitively defined in the present specification.

Figure 2:
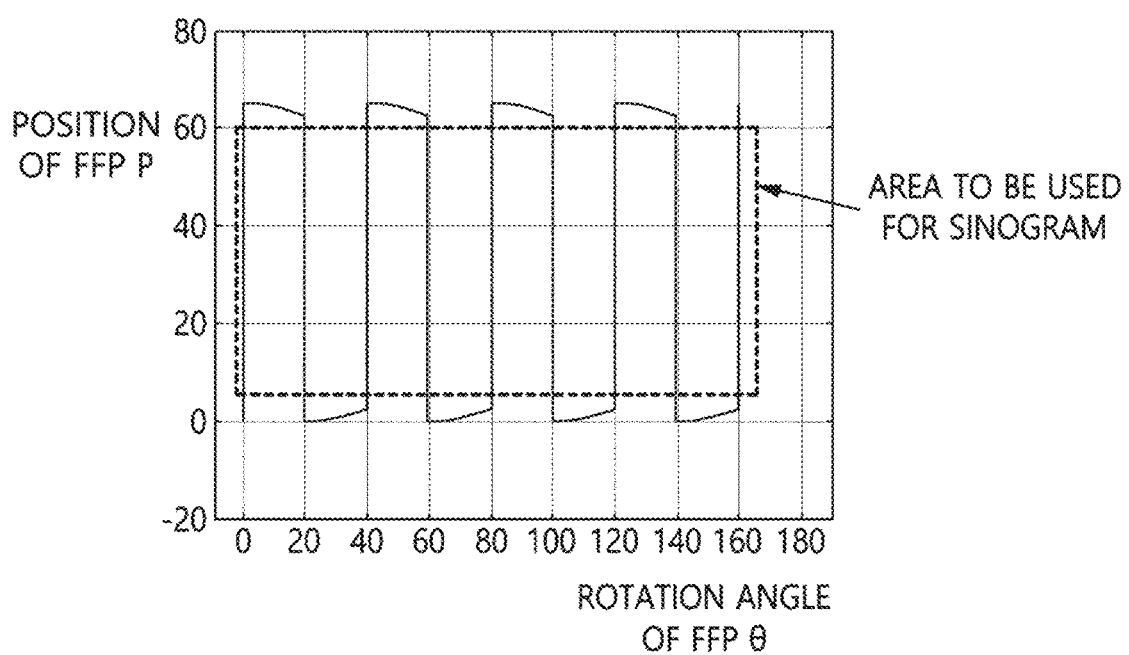
FIG. 2 is a view illustrating a sinogram generated by the operation illustrated in FIG. 1.

FIG. 1 is a view for explaining an operation for movement of a general field-free region, and FIG. 2 is a view illustrating a sinogram generated by the operation illustrated in FIG. 1.

Here, using a pair of magnets and a pair comprising a coil and a magnet, a gradient magnetic field generation unit generates a gradient magnetic field perpendicular to both pairs, and the graphs in FIG. 1 show values that are measured when the gradient magnetic field generation unit installed in a linear stage and a rotary stage is mechanically rotated and moved linearly.

Specifically, after a reciprocating linear motion or a forward linear motion is performed based on a unit angle of the rotary stage, the process of increasing the angle and performing a reciprocating linear motion or a backward linear motion is repeated until rotation through 180 degrees is complete. Among time-series data acquired during the linear motion, data pertaining to acceleration and deceleration sections is discarded, and only data pertaining to a uniform motion section is selected. Then, using the elapsed time, the position of an FFL is indirectly estimated and processed. Here, when a rotary step is narrowed in order to acquire a precise magnetic nanoparticle distribution image, the number of linear motions is increased in proportion to the total number of steps. Accordingly, the velocity of the linear motion is an important factor in determining the amount of time taken to capture an image.

Referring to FIG. 1, the linear stage is generally driven with a trapezoidal speed profile or an S-curve speed profile using a ball screw and an encoder motor. Here, because it is required to stop the motor and accelerate in the reverse direction at the end points of the stroke, the sum of the mass of the gradient magnetic field generation unit and the moment of rotational inertia of the motor for the moving direction component of the force of gravity on the mass acts as the applied load, which becomes a major obstacle to increasing the size of the gradient magnetic field generation unit so as to be appropriate for use with a human and to quick imaging of magnetic nanoparticles. Also, because an apparatus including the gradient magnetic field generation unit is required to additionally secure the distance traveled during acceleration and deceleration, the apparatus itself may have an unnecessarily large size. Here, when rapid deceleration, stopping, and rapid acceleration are repeated in order to minimize this distance, vibrations may be caused in the system.

Therefore, the present invention proposes an apparatus and method for imaging nano magnetic particles through which a small-sized and high-speed Magnetic Particle Imaging (MPI) system applicable to a human body may be realized by solving the problems of acceleration/deceleration load, vibration of the system, and unnecessary wasted space, which are caused when a reciprocating motion is performed using a linear stage.

Hereinafter, an apparatus and method for imaging nano magnetic particles according to an embodiment will be described in detail with reference to FIGS. 3 to 28.

Figure 3:
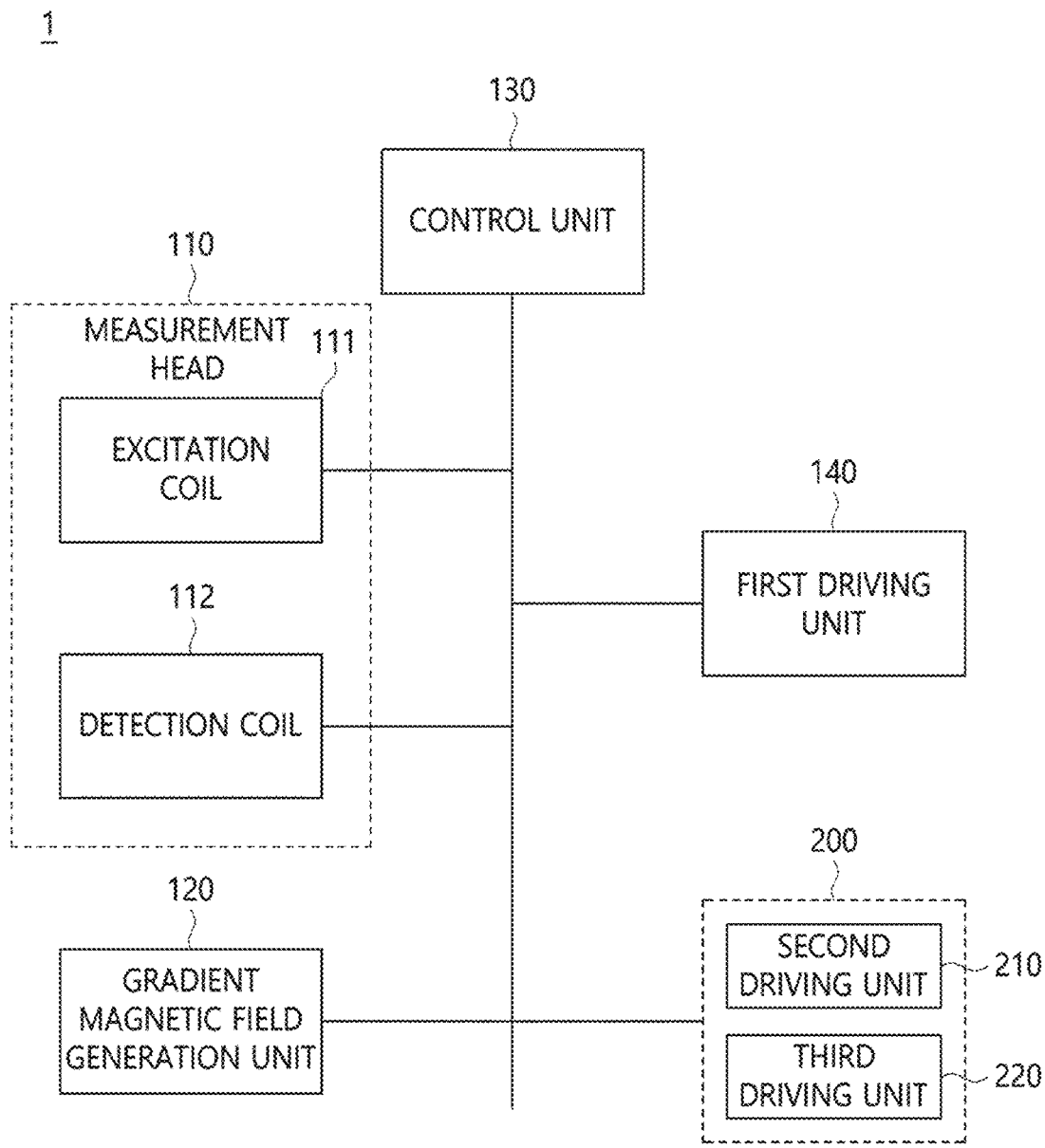
FIG. 3 is a schematic block diagram of an apparatus for imaging nano magnetic particles according to an embodiment.
Figure 4:
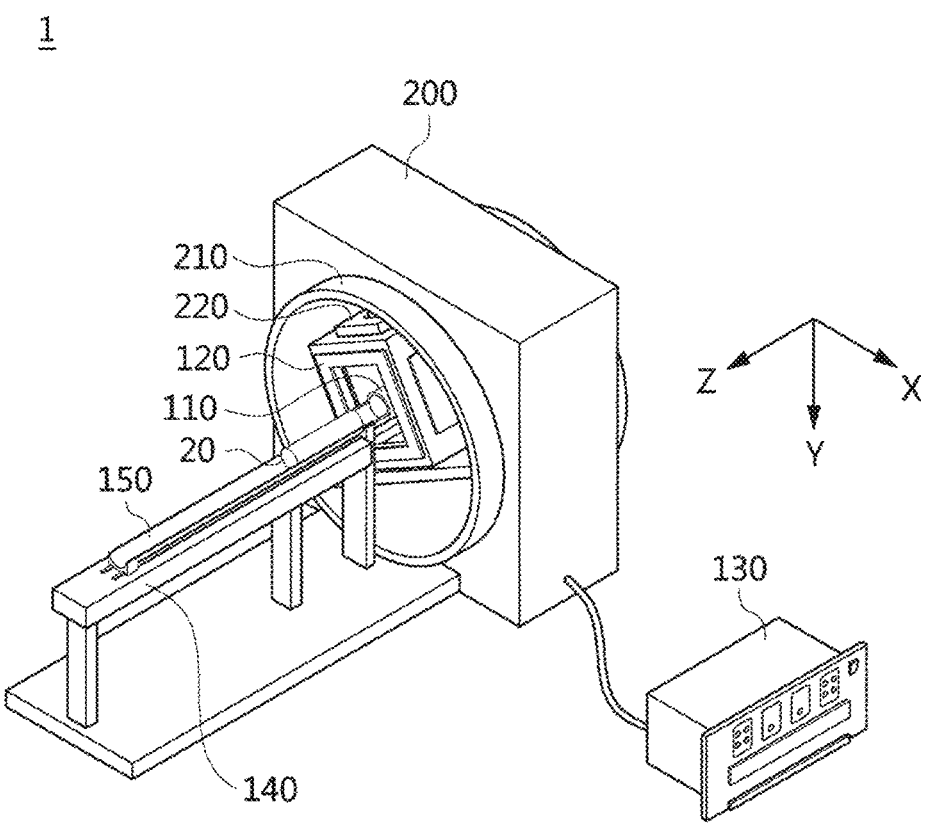
FIG. 4 is a view illustrating an example of the structure diagram of an apparatus for imaging nano magnetic particles according to an embodiment.

FIG. 3 is a schematic block diagram of an apparatus for imaging nano magnetic particles according to an embodiment, and FIG. 4 is a view illustrating an example of the structure diagram of an apparatus for imaging nano magnetic particles according to an embodiment.

Referring to FIG. 3, an apparatus 1 for imaging nano magnetic particles according to an embodiment includes a measurement head 110, a gradient magnetic field generation unit 120, a control unit 130, a first driving unit 140, a second driving unit 210, and a third driving unit 220.

In the measurement head 110, a through hole in which a sample including nano magnetic particles is accommodated is formed, and an excitation coil and a detection coil are installed. Here, the excitation coil generates a magnetic field in the measurement head 110, into which a sample including nano magnetic particles is inserted. Here, the detection coil may acquire a detection signal from the sample placed in the through hole in the measurement head 110. The measurement head will be described in detail later with reference to FIG. 5.

The gradient magnetic field generation unit 120 generates a magnetic field having a strength equal to or greater than the strength of the saturation magnetic field of the nano magnetic particles in a spacing area between identical magnetic poles facing each other, and forms a field-free region, in which there is a weak magnetic field or no magnetic field, in a portion of the spacing area.

Here, the basic principle of signal acquisition in Magnetic Particle Imaging (MPI) is based on a harmonic signal caused by nonlinear magnetic properties of Nano Magnetic Particles (NMP) in a gradient magnetic field. Here, two identical magnetic poles are oriented to face each other, which causes saturation without generation of a nonlinear magnetization phenomenon, whereby a field-free region is generated in a predetermined area of the spacing area.

Additionally, the field-free region is moved in the space, and imaging is realized using the location in space at which a harmonic signal is generated.

Here, the field-free region may be a Field-Free Point (FFP) or a Field-Free Line (FFL).

Here, the identical magnetic poles facing each other may be formed using at least one of a permanent magnet and a direct-current (DC) coil. Here, the permanent magnet may be a Neodymium magnet (N30 grade), Here, the identical magnetic poles facing each other may comprise two pairs.

Here, when the gradient magnetic field generation unit 120 is implemented using a permanent magnet, power for applying an electromagnetic field is not required. However, even in the case in which the gradient magnetic field generation unit 120 is implemented using a DC coil, the amount of power that is applied is minimal. Therefore, the amount of power consumed for 3D imaging of nano magnetic particles may be significantly reduced.

Meanwhile, as illustrated in FIG. 4, the gradient magnetic field generation unit 120 may be implemented such that a permanent magnet or a DC coil is mounted in a hexahedral housing in which an inner space is formed. However, the shape of the gradient magnetic field generation unit 120 illustrated in FIG. 4 is merely an embodiment, and the present invention is not limited thereto. Also, the structure of the gradient magnetic field generation unit 120 will be described in detail later with reference to FIGS. 6 to 9.

The first driving unit 140 linearly moves a sample bed 150 in a direction in the spacing area. Here, the direction may be, for example, the Z-axis direction illustrated in FIG. 4. The structure of the first driving unit 140 will be described in detail later with reference to FIG. 10 and FIG. 11.

The second driving unit 210 rotates the gradient magnetic field generation unit 120 in a plane perpendicular to the direction. Here, the plane may be, for example, parallel to the XY plane illustrated in FIG. 4. The structure of the second driving unit 210 will be described in detail later with reference to FIG. 12.

The third driving unit 220 causes the gradient magnetic field generation unit 120 to linearly reciprocate in a plane by converting rotation into sinusoidal reciprocation. The structure of the third driving unit 220 will be described in detail later with reference to FIGS. 13 to 20.

The control unit 130 controls the overall process of imaging of nano magnetic particles by controlling the components. Here, the control unit 130 may include any of all types of devices capable of processing data, such as a processor. Here, the term 'processor' may indicate, for example, a data-processing device embedded in hardware, which has a physically structured circuit in order to perform a function expressed using code or instructions included in a program.

According to an embodiment, when the measurement head 110 is located in the spacing area of the gradient magnetic field generation unit 120, the control unit 130 may apply a signal to the excitation coil, may control the first driving unit 140, the second driving unit 210, and the third driving unit 220 so as to move a field-free region in a sample, and may image the 3D positional distribution of the nano magnetic particles included in the sample based on a detection signal output from the detection coil. According to an embodiment, the control unit 130 performs control so as to continuously move the FFP or FIT and arranges the detection signals, which are detected when the sample overlaps the FFP or FFL, thereby acquiring 3D image information corresponding to the nano magnetic particles. For example, the 3D image information may include stereoscopic image information in the form of a contour plot.

Here, the control unit 130 may generate a 2D image, which is the 2D positional distribution of the nano magnetic particles included in the cross section of the sample, based on the detection signal, and may generate a 3D image by synthesizing multiple 2D images corresponding to multiple cross sections that are parallel to each other. Here, the cross section of the sample may, for example, be parallel to the XY plane illustrated in FIG. 4.

Here, the control unit 130 performs control so as to repeat the rotation of the gradient magnetic field generation unit 120 by the second driving unit 210 and the linear reciprocation of the gradient magnetic field generation unit 120 by the third driving unit 220, generates a sinogram using a signal output from the detection signal according to the movement of the field-free region, and performs inverse radon transformation on the generated sinogram, thereby generating a 2D image.

Here, the sinogram is sequential arrangement of projection data, acquired from one direction, in the projection direction. In the sinogram, pixel values in each row match the amplitude of the corresponding profile at the corresponding position. The sinogram is a well-known art, and thus a detailed description thereof will be omitted. Also, the inverse radon transform is a 2D image generation method using a sinogram, which is widely used for CT or the like, and is technology published in a paper written by Kak, A. C., and M. Slaney and titled "Principles of Computerized Tomographic Imaging" (New York, N.Y., IEEE press, 1988). Therefore, a detailed description thereof will be omitted.

For example, referring to FIG. 4, the field-free region may be rotated by the predetermined unit angle in the XY plane, or may be linearly moved in the state in which it has been rotated. This may be referred to as T-round stage movement.

Here, the control unit 130 may control the second driving unit 210 so as to intermittently rotate the gradient magnetic field generation unit 120, and may delete data acquired during rotation from a sinogram generated as the result of intermittent rotation.

Here, the control unit 130 may control the second driving unit 210 so as to continuously rotate the gradient magnetic field generation unit 120, and may generate a sinogram through 2D interpolation of a detection signal that is acquired as the result of continuous rotation.

Also, the control unit 130 may repeat generation of a 2D image while moving the sample bed 150 by a predetermined unit length in a direction perpendicular to the cross section of the sample. That is, the sample bed 150 is linearly moved in the Z-axis direction by the first driving unit 140, whereby 2D images for the respective cross sections through which the field-free region passes may be acquired.

Also, the apparatus 1 for imaging nano magnetic particles according to an embodiment of the present invention may include an interface unit (not illustrated), which is able to output an image of nano magnetic particles and receive a control selection for imaging the nano magnetic particles from a manipulator, or may be connected with the interface unit. The interface unit may include both an input function and an output function. For example, the input unit may be provided through a keyboard, a mouse, or any of various methods such as sound recognition and the like, and the output unit may be provided through a projector, various types of display panels, sound, vibration, or the like. Also, the input unit and the output unit may be implemented together in the form of a single touch panel.

Figure 5:
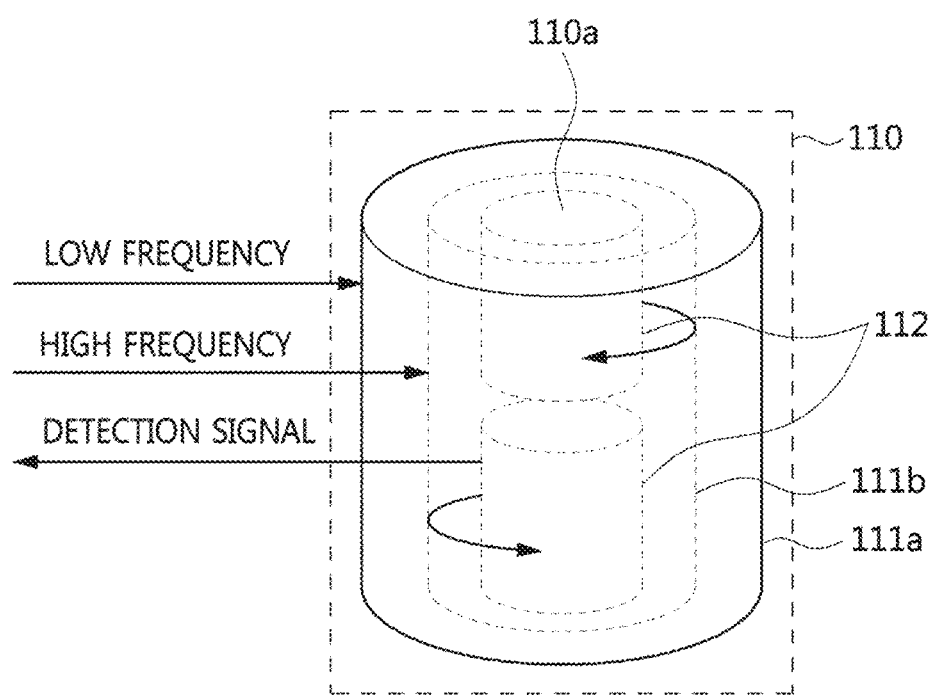
FIG. 5 is an exemplary view simply illustrating the structure of coils of a measurement head according to an embodiment.

FIG. 5 is an exemplary view simply illustrating the structure of a coil of a measurement head according to an embodiment.

Referring to FIG. 5, the measurement head 110 may include excitation coils 111*a* and 111*b* and a detection coil 112.

Here, each of the excitation coils 111*a* and 111*b* is a solenoid coil for generating a magnetic field, and a mixed magnetic field in which the two magnetic fields generated from the respective excitation coils are mixed may be generated.

Here, the excitation coils 111*a* and 111*b* may be a low-frequency coil 111*a* and a high-frequency coil 111*b*, respectively.

Here, the low-frequency coil 111*a* may be located on the outermost side of the measurement head 110, the high-frequency coil 111*b* may be located in the interior of the low-frequency coil 111*a*, and the detection coil 112 may be located in the interior of the high-frequency coil 111*b*. That is, the measurement head 110 includes the low-frequency coil 111*a* and the high-frequency coil 111*b* and generates a magnetic field using a low-frequency signal and another magnetic field using a high-frequency signal, thereby generating a mixed magnetic field.

Also, the low-frequency coil 111*a* may receive a signal applied from a power source corresponding to a low-frequency voltage, and the high-frequency coil 111*b* may receive a signal applied from a power source corresponding to a high-frequency voltage.

Here, the electromotive force output by the detection coil 112 may be a detection signal. Here, the detection coil 112 may be a differential detection coil formed by connecting two coils that are wound in different directions. Therefore, a combination of signals detected from the two coils, which are wound in different directions, may be acquired as a detection signal in the detection coil 112.

Accordingly, in order to acquire a harmonic signal on the nonlinear FFL or FFP, two different frequencies are used in the excitation coils, and simultaneously, one side of the differential coil is saturated with a strong magnetic field, whereby the situation in which signals are output from all mutually opposing sides of the detection coil may be declined while maintaining the effect of differential detection.

Figure 6:
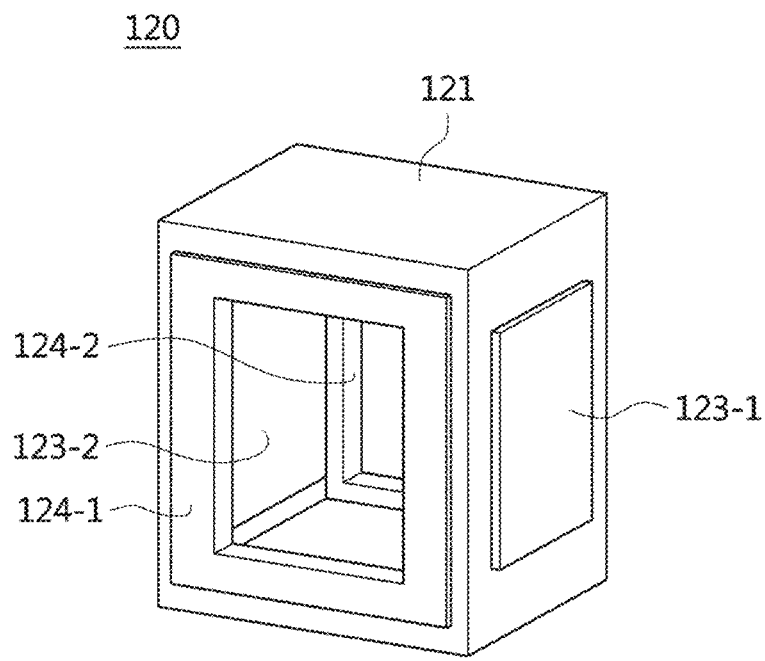
FIG. 6 is an example of the structure diagram of a gradient magnetic field generation unit according to an embodiment.
Figure 7:
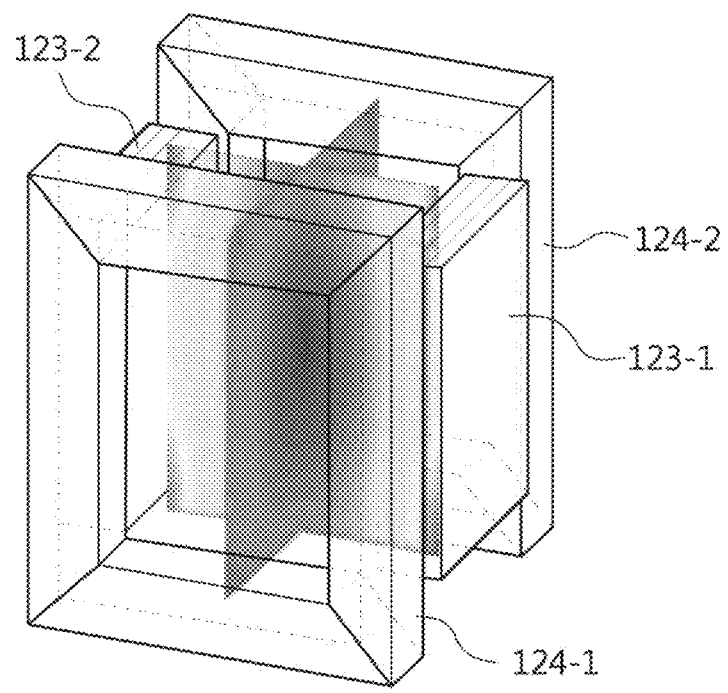
FIG. 7 is an exemplary view of a gradient magnetic field generated by the gradient magnetic field generation unit illustrated in FIG. 6.

FIG. 6 is an example of the structure diagram of a gradient magnetic field generation unit according to an embodiment, and FIG. 7 is an exemplary view of a gradient magnetic field generated by the gradient magnetic field generation unit illustrated in FIG. 6.

Referring to FIG. 6, the gradient magnetic field generation unit 120 may include a hexahedral housing 121, and the housing 121 may have a through hole passing through the housing in one direction. Accordingly, the measurement head 110 may be inserted and accommodated in the housing 121.

The gradient magnetic field generation unit 120 may generate a magnetic field having a strength equal to or greater than the strength of the saturation magnetic field of nano magnetic particles in a spacing area between identical magnetic poles facing each other, and may form a field-free region, in which there is a weak magnetic field or no magnetic field, in a portion of the spacing area.

Here, the identical magnetic poles facing each other may be formed using a pair of permanent magnets 123-1 and 123-2 that generate a gradient magnetic field in a plane, as illustrated in FIG. 6 and FIG. 7.

Here, the identical magnetic poles facing each other ma be further formed using a pair of DC coils 124-1 and 124-2 that generate a gradient magnetic field in another plane perpendicular to the plane, as illustrated in FIG. 6 and FIG. 7. Here, the pair of DC coils 124-1 and 124-2 may generate a magnetic field having a strength equal to or greater than that of the saturation magnetic field of the magnetic nano particles on one side of the measurement head 110.

Here, each of the DC coils 124-1 and 124-2 is a solenoid coil having about 1000 turns of a coil of about 1.3 mm, and DC power may be applied thereto.

Here, when the permanent magnets 123-1 and 123-2 are placed such that the N poles thereof face each other, the direction of current applied to the DC coils 124-1 and 124-2 may be controlled such that the S poles thereof face each other.

Figure 8:
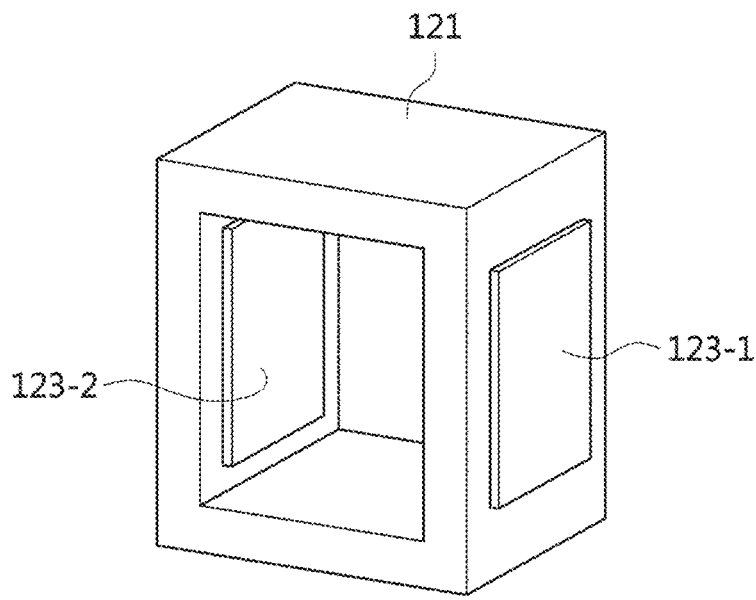
FIG. 8 is another example of the structure diagram of a gradient magnetic field generation unit according to an embodiment.
Figure 9:
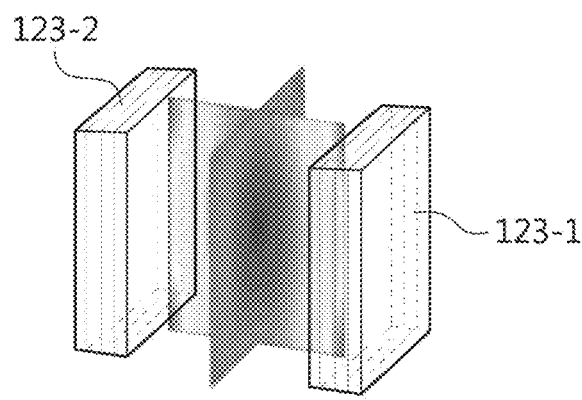
FIG. 9 is an exemplary view of a gradient magnetic field generated by the gradient magnetic field generation unit illustrated in FIG. 8.

FIG. 8 is another example of the structure diagram of a gradient magnetic field generation unit according to an embodiment, and FIG. 9 is an exemplary view of a gradient magnetic field generated by the gradient magnetic field generation unit illustrated in FIG. 8.

Referring to FIG. 8 and FIG. 9, unlike what is illustrated in FIG. 6 and FIG. 7, the gradient magnetic field generation unit 120 may include only a pair of permanent magnets 123-1 and 123-2 that generate a gradient magnetic field in a plane. That is, when magnetic nanoparticles having a sufficiently low saturation magnetic field are used in a sample, a pair of DC coils 124-1 and 124-2 may not be required.

Figure 10:
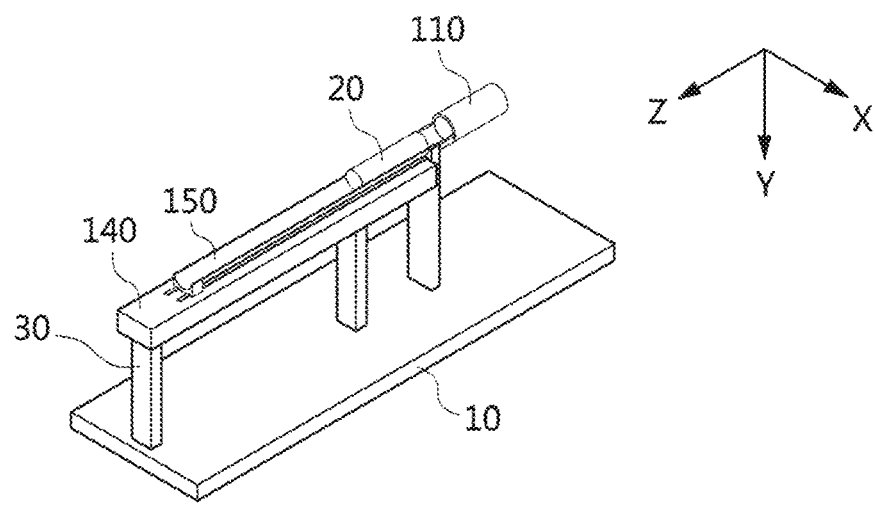
FIG. 10 is an exemplary view of the structure of a first driving unit according to an embodiment.
Figure 11:
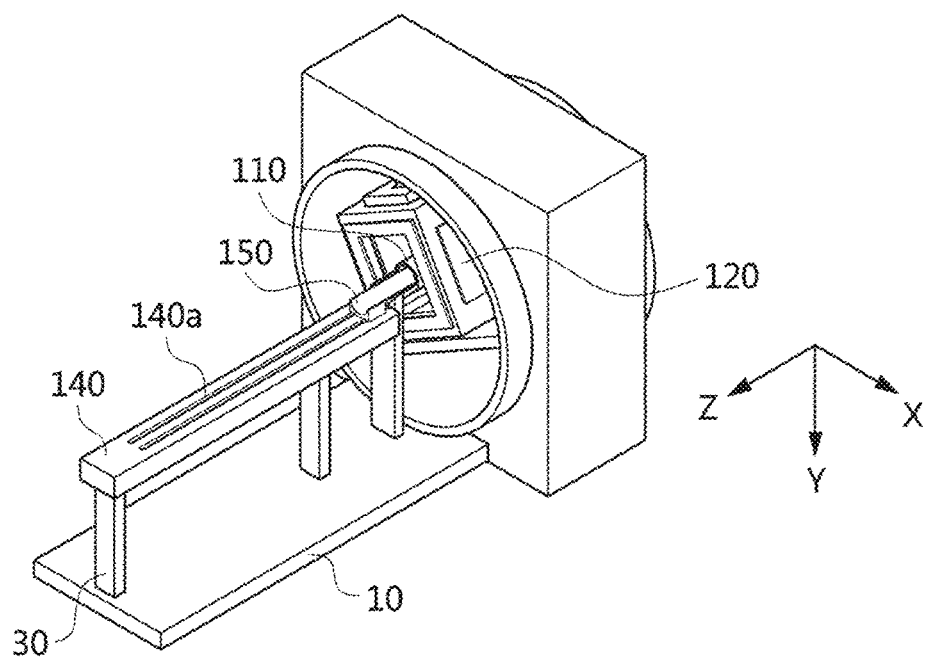
FIG. 11 is a view for explaining the operating state of a first driving unit according to an embodiment.

FIG. 10 is an exemplary view of the structure of a first driving unit according to an embodiment, and FIG. 11 is a view for explaining the operating state of the first driving unit according to an embodiment.

Referring to FIG. 10 and FIG. 11, the first driving unit 140 may be installed on a support 30 in the form of a table placed on a base 10. Here, the first driving unit 140 may be installed at a location, the height of which matches the height of the gradient magnetic field generation unit 120, so as to enable a sample bed 150 to be inserted into the gradient magnetic field generation unit 120.

Here, the first driving unit 140 includes a linear guide 140*a* that is formed parallel to the Z-axis, and the sample bed 150 may be linearly moved along the linear guide 140*a*.

Here, the sample bed 150 is formed such that the upper portion thereof has a semi-cylindrical concave surface, whereby the sample 20 may be moved along with the sample bed 150 and inserted into the measurement head 110.

Figure 12:
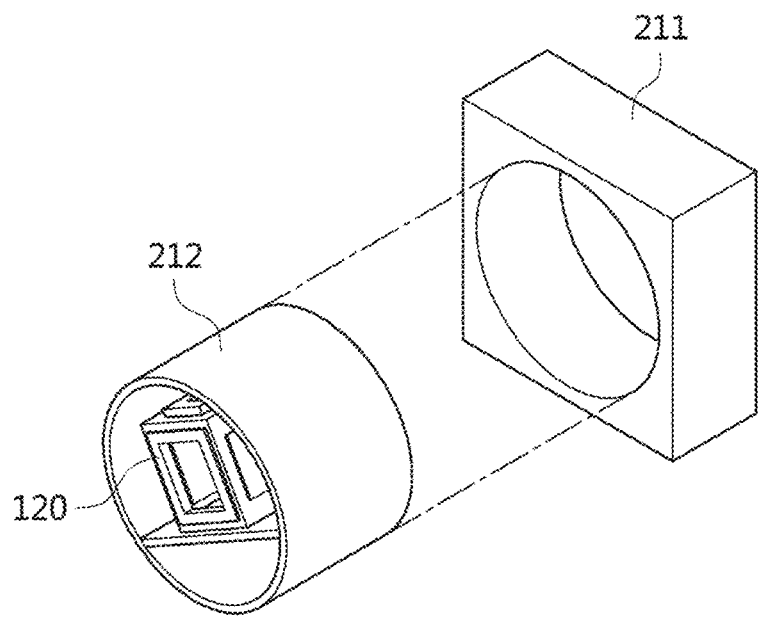
FIG. 12 is an exemplary view of the structure of a second driving unit according to an embodiment.
Figure 13:
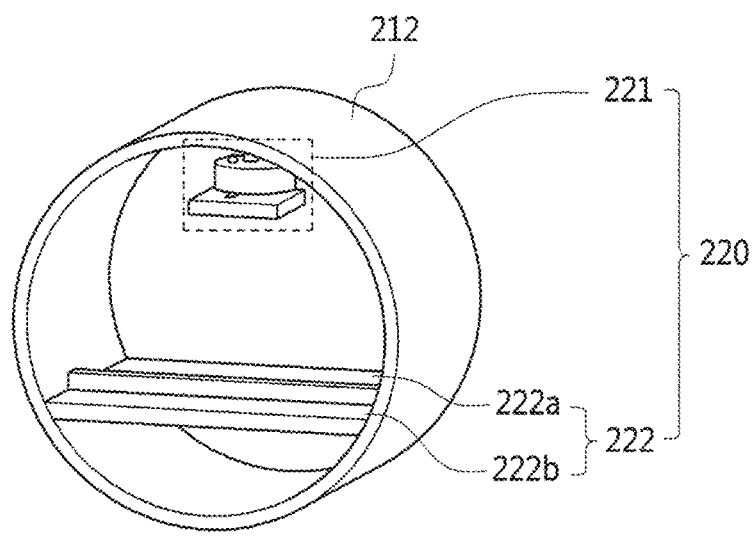
FIG. 13 is an exemplary view of the structure of a third driving unit according to an embodiment.
Figure 14:
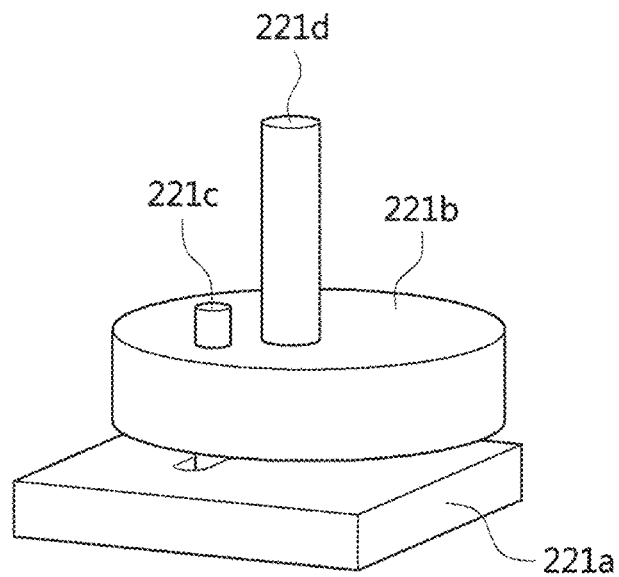
FIG. 14 is an example of a perspective view of a scotch yoke when viewed from above according to an embodiment.
Figure 15:
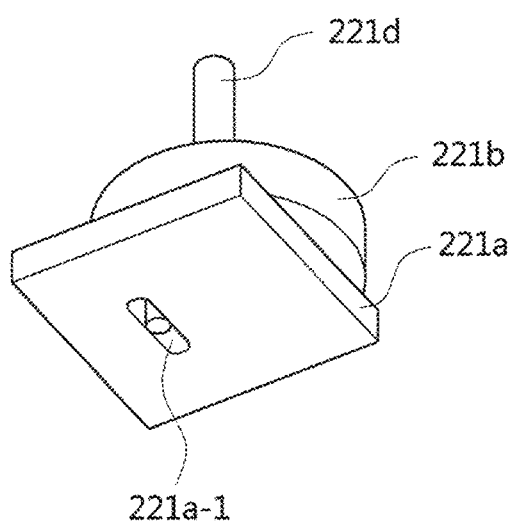
FIG. 15 is an example of a perspective view of a scotch yoke when viewed from below according to an embodiment.
Figure 16:
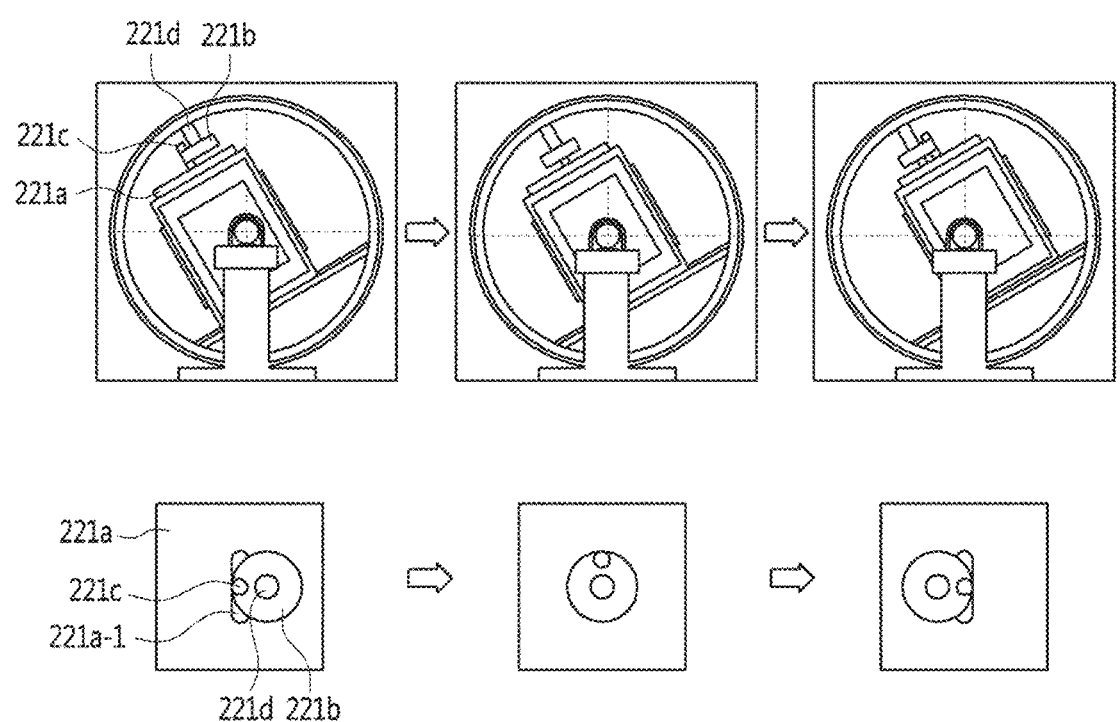
FIG. 16 is an exemplary view for explaining the operation of a third driving unit according to an embodiment.

FIG. 12 is an exemplary view of the structure of a second driving unit according to an embodiment, FIG. 13 is an exemplary view of the structure of a third driving unit according to an embodiment, FIG. 14 is an example of a perspective view of a scotch yoke viewed from above according to an embodiment, FIG. 15 is an example of a perspective view of the scotch yoke viewed from below according to an embodiment, and FIG. 16 is an exemplary view for explaining the operation of the third driving unit according to an embodiment.

Referring to FIG. 12, the second driving unit 120 may include a support 211, in which a through hole is formed, and a rotation part 212 that is formed in a cylindrical shape to be inserted into the through hole. The rotation part 212 may accommodate the gradient magnetic field generation unit 120 by joining the same to the inner side thereof.

Here, a first motor (not illustrated) for rotating the rotation part 212 in response to a control signal input from the control unit 130 may be included. Here, the first motor may be a servomotor including a decelerator.

Here, the apparatus for imaging nano magnetic particles according to an embodiment may further include a first detection unit (not illustrated) for measuring the reference point of the rotation part 212 or the rotation angle thereof.

Here, the rotation part 212 may further include a linear guide 222 joined to the gradient magnetic field generation unit 120 on the inner side thereof, thereby guiding the gradient magnetic field generation unit 120 so as to linearly move in a plane, as illustrated in FIG. 13.

Also, the third driving unit 220 may be a scotch yoke 221, which is formed by being joined between the inner side of the rotation part 212 and the gradient magnetic field generation unit 120, as illustrated in FIG. 13, and which causes the gradient magnetic field generation unit 120 to linearly reciprocate along the linear guide 222 by converting rotation into sinusoidal reciprocation.

Here, although not illustrated in the drawings, the rotation part 212 may include slip rings, which are capable of supplying power even during continuous rotation, in order to supply the power required for the third driving unit 220 and the pair of DC coils 124-1 and 124-2 of the gradient magnetic field generation unit 120.

Here, when the pair of DC coils 124-1 and 124-2 is not required, as illustrated in FIG. 8 and FIG. 9, dedicated slip-rings (not illustrated) may also not be required. In this case, because only a common slip ring for supplying power required for driving the scotch yoke 221 is installed in the rotation part 212, it may be advantageous for the gradient magnetic field generation unit 120 to continuously rotate in one direction in a plane.

Here, the scotch yoke 221 may be fixed to the gradient magnetic field generation unit 120, as illustrated in FIGS. 14 to 15, and may include a sliding yoke 221a with a slot 221a-1, which is formed to be perpendicular to the transfer direction of the linear guide 222, a crank 221b integrated with an eccentric crank pin 221c that engages the slot 221a-1, and a second motor 221d for supplying torque to the center of the crank 221b.

Here, the second motor 221d may be a servomotor including a decelerator (not illustrated). Also, the eccentric crank pin 221c may be freely moved within the border of the slot 221a-1 without friction or a gap therebetween.

Here, the apparatus for imaging nano magnetic particles according to an embodiment may further include a second detection unit (not illustrated) for measuring the reference point of the central axis of the crank 221b or the rotation angle of the central axis.

Referring to FIG. 14, when motive power (torque) from the second motor 221d is input to the torque input axis of the crank 221b, the eccentric crank pin 221c integrated therewith is caused to perform eccentric rotational motion on the torque input axis. As the result of the eccentric rotational motion that draws a radius corresponding to the amount of eccentricity of the eccentric crank pin 221c, the sliding yoke 221a, into which the eccentric crank pin 221c is inserted, is caused to perform linear reciprocating motion with a sinusoidal position profile.

Accordingly, the gradient magnetic field generation unit 120 may also be caused to perform linear reciprocating motion with a sinusoidal position profile. Here, based on the linear motion with a sinusoidal position profile, all of velocity, acceleration, and jerk, which is derived from acceleration based on time, can be differentiated, whereby stable driving may be achieved without causing vibration.

Meanwhile, the mass of the crank 221b may be equivalent to the mass of the gradient magnetic field generation unit 120.

When the rotation part 212 rotates by an angle close to 90 degrees, the gradient magnetic field generation unit 120 is required to move opposite the direction of gravity, and thus the load imposed on the second motor 221d of the scotch yoke 221 is maximized.

Figure 17:
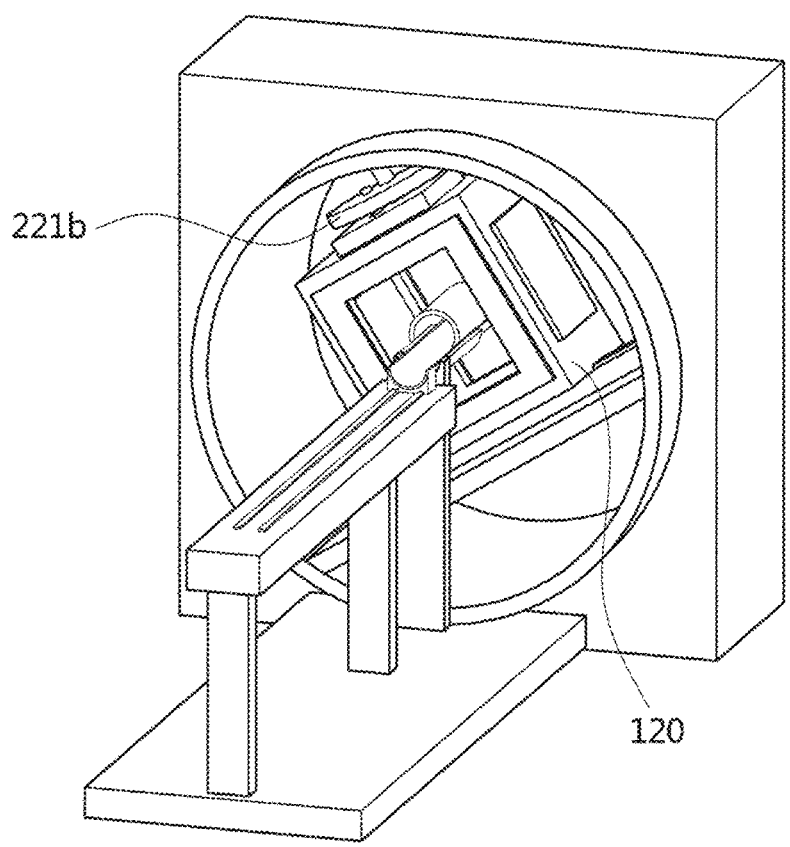
FIG. 17 and FIG. 18 are views for explaining an example in which a crank is used as a flywheel.
Figure 18:
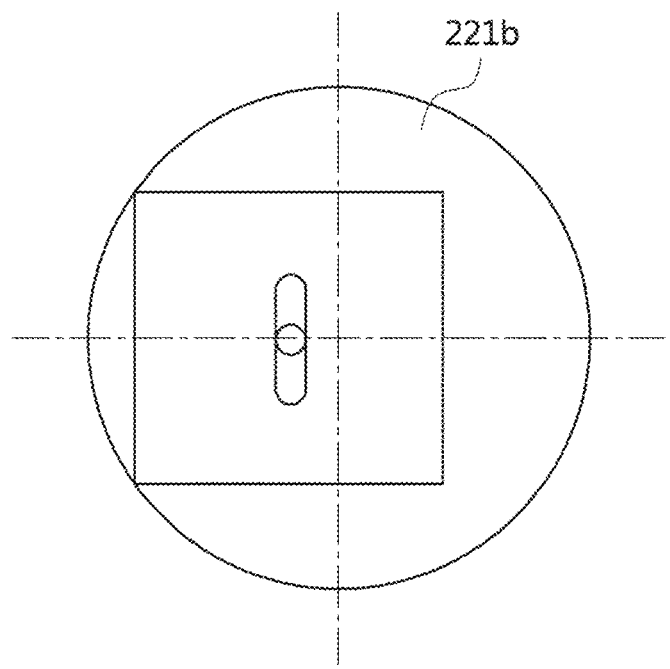

In order to solve this problem, the crank 221b may be used as a flywheel, the moment of rotational inertia of which is increased, according to an embodiment. This makes it disadvantageous to accelerate at first, but is advantageous in maintaining constant power output from the second motor 221d regardless of the rotation angle of the rotation part 212 and the location of the gradient magnetic field generation unit 120. FIG. 17 and FIG. 18 are views for explaining an example in which the crank is used as a flywheel.

Figure 19:
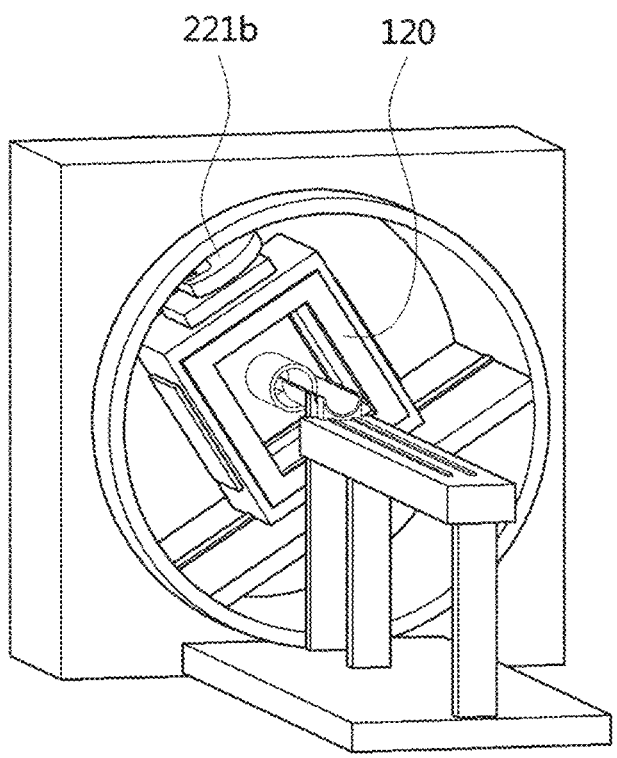
FIG. 19 and FIG. 20 are view for explaining an example in which a crank is used as a counterweight.
Figure 20:
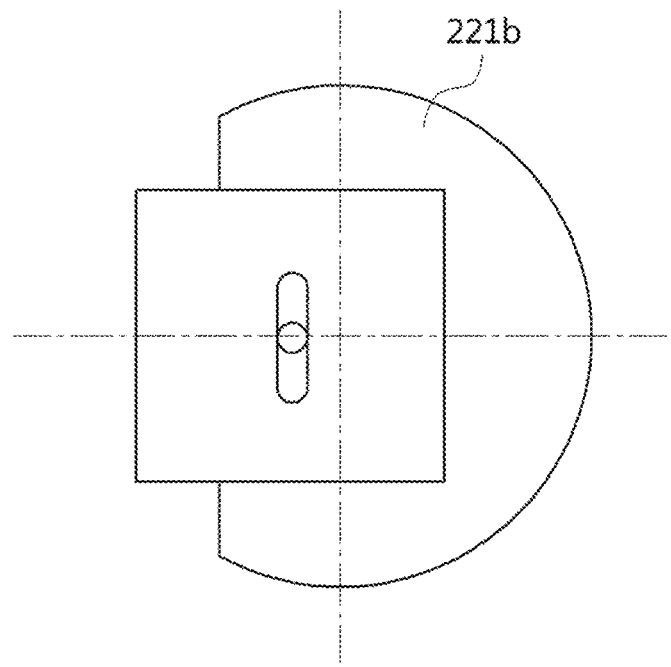

Meanwhile, in order to reduce the amount of torque required for a low-speed elevation operation of the gradient magnetic field generation unit 120, an eccentric mass equal to the total mass of the gradient magnetic field generation unit 120 may be implemented in the crank 221b of the scotch yoke. FIG. 19 and FIG. 20 are views for explaining an example in which the crank is used as a counterweight.

Figure 21:
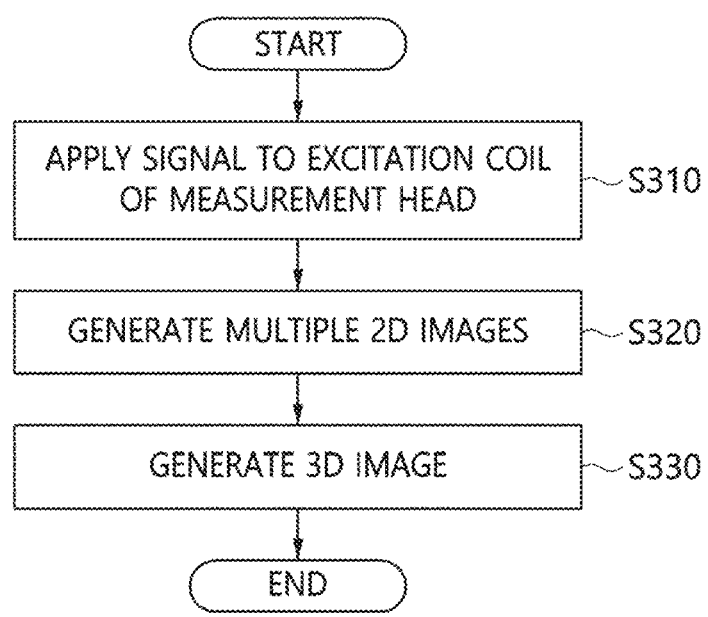
FIG. 21 is a flowchart for explaining a method for imaging magnetic particles according to an embodiment.

FIG. 21 is a flowchart for explaining a method for imaging magnetic particles according to an embodiment. Here, the method for imaging magnetic particles is performed by the apparatus for imaging magnetic particles described with reference to FIGS. 1 to 20, and a repeated description will be omitted.

Referring to FIG. 21, the method for imaging nano magnetic particles according to an embodiment may include applying a signal to an excitation coil installed in a measurement head that accommodates a sample including nano magnetic particles at step S310 and generating a magnetic field having a strength equal to greater than that of the saturation magnetic field of the nano magnetic particles in a spacing area between identical magnetic poles facing each other, moving a field-free region formed in a portion of the spacing area in the sample, and imaging the 3D positional distribution of the nano magnetic particles included in the sample based on a detection signal output from the detection coil of the measurement head at steps S320 to S330.

Here, the field-free region may be linearly moved in one direction, may be rotated in a plane perpendicular to the one direction, or may be caused to linearly reciprocate in the plane by converting rotation into sinusoidal reciprocation.

Here, imaging the 3D positional distribution of the nano magnetic particles may include generating a 2D image, which is the 2D positional distribution of nano magnetic particles included in a cross section of the sample, based on the detection signal at step S320 and generating a 3D image by synthesizing multiple 2D images corresponding to multiple cross sections that are parallel to each other at step S330.

Generating the 2D image at step S320 may include repeatedly performing rotation and linear reciprocation of the field-free region, generating a sinogram using a signal that is output from the detection signal according to the movement of the field-free region, and generating a 2D image by performing inverse radon transform on the generated sinogram.

Figure 22:
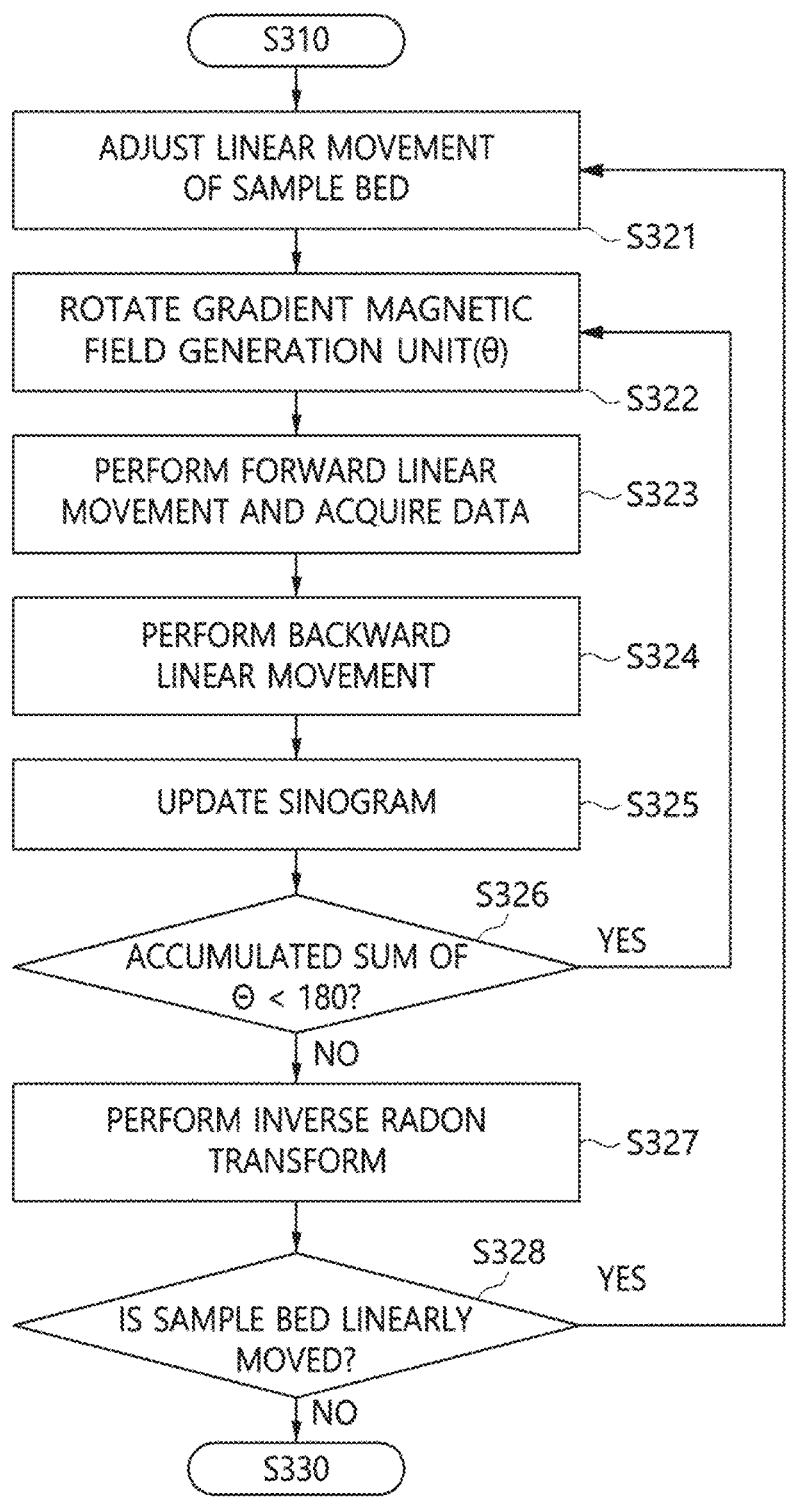
FIG. 22 is a flowchart for explaining the 2D image generation step of FIG. 21 in detail.

FIG. 22 is a flowchart for explaining the 2D image generation step of FIG. 21 in detail.

Referring to FIG. 22, first, the control unit 130 adjusts linear movement of the sample bed 150 at step S321. That is, the position of the sample on the Z-axis is adjusted. At the outset, the position is adjusted such that the FFL or FFP passes through the peak or bottom point of the sample.

Then, the control unit 130 rotates the rotation part 212 by θ degrees, which is a predetermined angle, at step S322. That is, the FFL or FFP generated by the gradient magnetic field generation unit 120 is rotated by θ degrees in one cross section of the sample (XY plane).

The control unit 130 continuously causes the gradient magnetic field generation unit 120 to linearly move forwards (forward linear movement) and acquires a signal detected by the detection coil 112 at predetermined unit time intervals at step S323. Then, the control unit 130 causes the gradient magnetic field generation unit 120 to linearly move backwards (backward linear movement) by the distance of the forward linear movement, thereby returning the gradient magnetic field generation unit 120 to its original position at step S324.

Here, according to an embodiment, rotation is converted into sinusoidal reciprocation, whereby the gradient magnetic field generation unit 120 is caused to linearly reciprocate in a cross section.

Then, the control unit 130 updates a sinogram, which is capable of representing a predetermined image signal, based on the signal output from the detection coil 112 at step S325.

Then, the control unit 130 determines whether the accumulated sum of the rotated angle θ is less than 180 degrees at step S326.

When it is determined at step S326 that the accumulated sum of the rotated angle θ is less than 180 degrees, the control unit 130 performs control so as to repeatedly perform steps S322 to S325. Conversely, when it is determined at step S326 that the accumulated sum of the rotated angle θ is not less than 180 degrees, the control unit 130 performs inverse radon transformation on the generated sinogram, thereby realizing 2D imaging of the cross section (XY plane) of the sample at the current height at step S327.

Then, the control unit 130 repeatedly performs steps S321 to S327 depending on the result of the determination of whether the sample bed is linearly moved at step S328.

Meanwhile, according to the present invention, generating the 2D image at step S320 may be implemented through various embodiments.

According to an embodiment, generating the 2D image at step S320 may be configured to intermittently rotate the field-free region and to delete data acquired during rotation from the sinogram generated as the movement of the field-free region.

Figure 23:
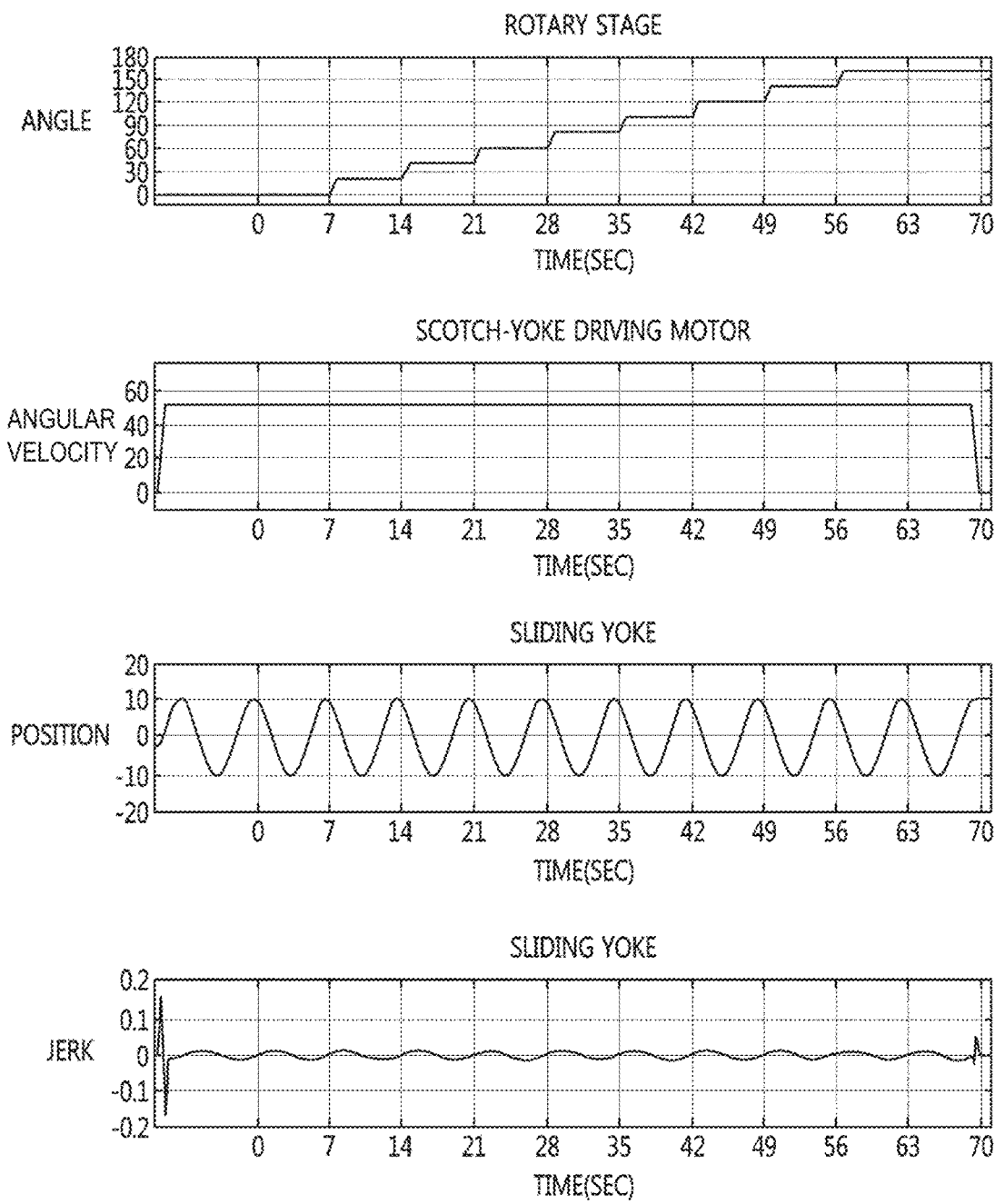
FIG. 23 and FIG. 24 are views for explaining 2D image generation according to an embodiment of the present invention.
Figure 24:
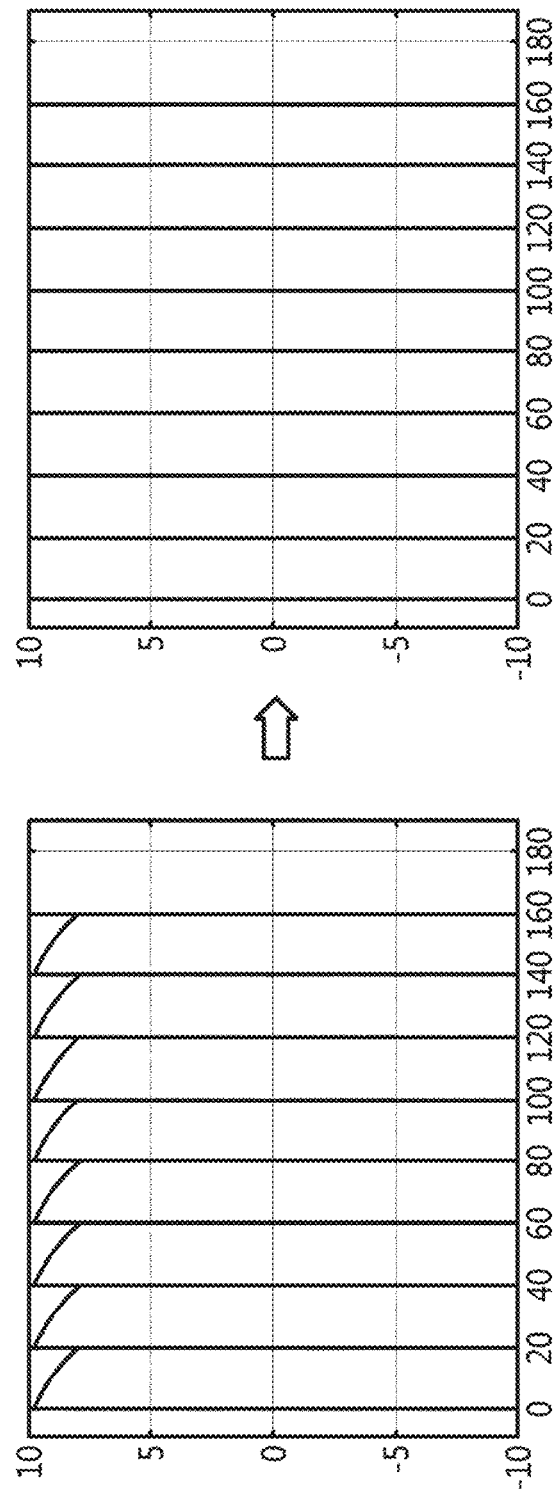

FIG. 23 and FIG. 24 are views for explaining 2D image generation according to an embodiment of the present invention.

Referring to FIG. 23, according to an embodiment, the control unit 130 may intermittently and slowly rotate the rotation part 212 at step S322 illustrated in FIG. 22.

To this end, the control unit 130 may adjust the angular velocity of the second motor 221d of the scotch yoke 221 at steps S323 and S324. That is, when the rotation part 212 is intermittently and slowly rotated, the control unit 130 changes the rotation angle of the rotation part 212 after the sliding yoke reciprocates by one period of a sine wave.

That is, after the acceleration of the second motor 221d is finished, the sliding yoke is capable of reciprocating without applying a sudden jerk to the gradient magnetic field generation unit.

Referring to FIG. 24, because both the angle of the FFL, represented on the horizontal axis of the sinogram, and the position of the FFL, represented on the vertical axis of the sinogram, are functions of time, the sinogram illustrated on the right side may be generated using the measurement values illustrated on the left side. Here, the sinogram illustrated on the left side includes a trajectory in which horizontal axes are connected to each other.

Accordingly, in an embodiment, the control unit 130 deletes the connection trajectory at step S325 illustrated in FIG. 22, whereby the sinogram on which inverse radon transform is to be performed may be acquired.

Meanwhile, according to another embodiment, generating the 2D image at step S320 may be configured to continuously rotate the field-free region and to interpolate the detection signal, which is acquired as the result of movement of the field-free region, in 2D, whereby a sinogram may be generated.

Figure 25:
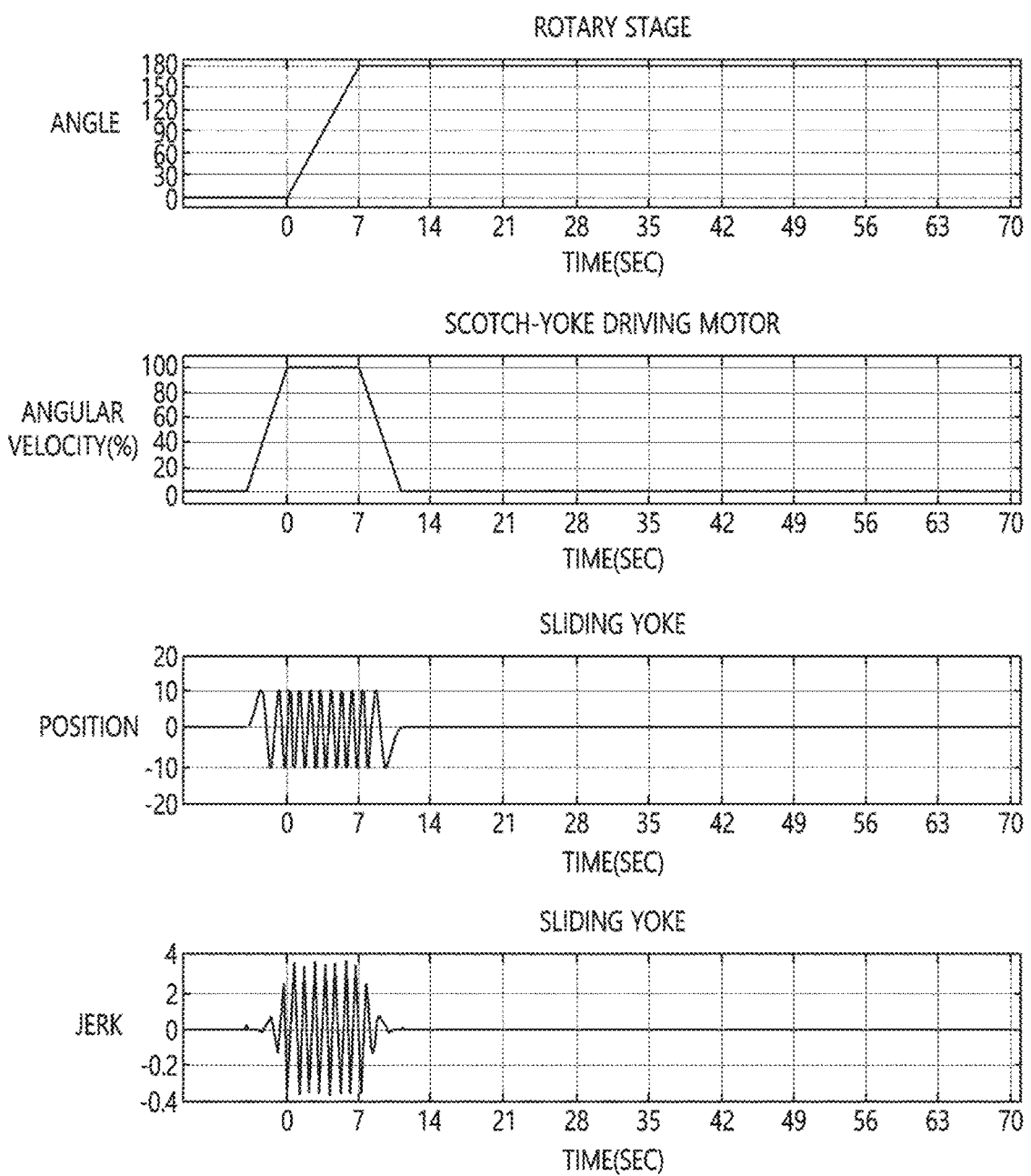
FIG. 25 and FIG. 26 are views for explaining 2D image generation according to an embodiment of the present invention.
Figure 26:
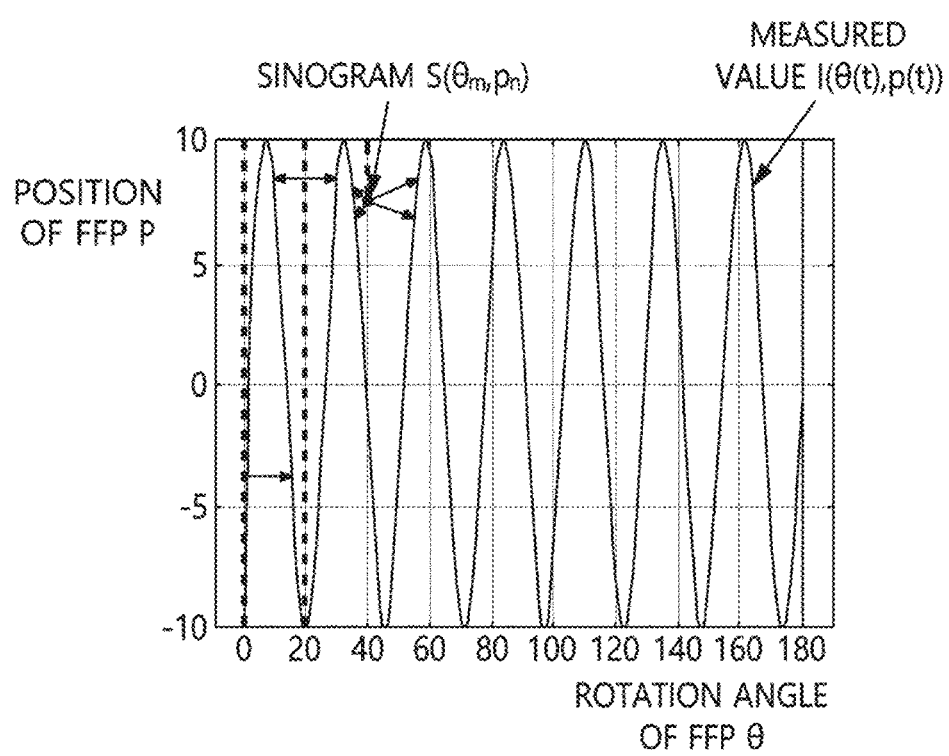

FIG. 25 and FIG. 26 are views for explaining 2D image generation according to another embodiment of the present invention.

Referring to FIG. 25, according to another embodiment, the control unit 130 may continuously rotate the rotation part 212 rapidly at step S322 illustrated in FIG. 22.

To this end, the control unit 130 may adjust the angular velocity of the second motor 221d of the scotch yoke 221 at steps S323 and S324. That is, when the rotation part 212 is continuously rotated rapidly, the control unit 130 may increase the angular velocity of the second motor 221d such that the sliding yoke reciprocates with a sinusoidal motion a predetermined number of times while the rotation part 212 is continuously rotated.

Accordingly, when the control unit 130 continuously quickly rotates the rotation part 212 with a constant velocity at step S322 illustrated in FIG. 22, a transient response is avoided, and a discontinuous jerk is caused in the sliding yoke only when the rotation part 212 is initially driven, whereby high-speed driving may be realized without a transient response during the overall process.

Referring to FIG. 26, according to another embodiment, the control unit 130 may arrange the measured value I(θ(t), p(t)) in the 2D space (like the solid line in the sinogram) for a value I(t) at step S325 illustrated in FIG. 22, and may calculate a pixel value $S(\theta_m, P_n)$ of the sinogram, which is to be used for inverse radon transform, through interpolation using actually measured data I(θ(t), p(t)) adjacent thereto, that is, using one, two, or four pixel values located adjacent thereto in the upward, downward, leftward and rightward directions with respect to the pixel location ($\theta_m$, $P_m$) of the pixel value S($\theta_m$, $P_n$).

According to a further embodiment of the present invention, generating the 2D image at step S320 is configured to continuously rotate the field-free region by an angle equal to or greater than 360 degrees while consecutively linearly moving the sample bed 150 accommodating the sample with a constant velocity, to arrange the is detection signal acquired therefrom in 3D, and to perform interpolation using adjacent points in the space, thereby generating a 2D sinogram of an arbitrary cross section of the sample.

Figure 27:
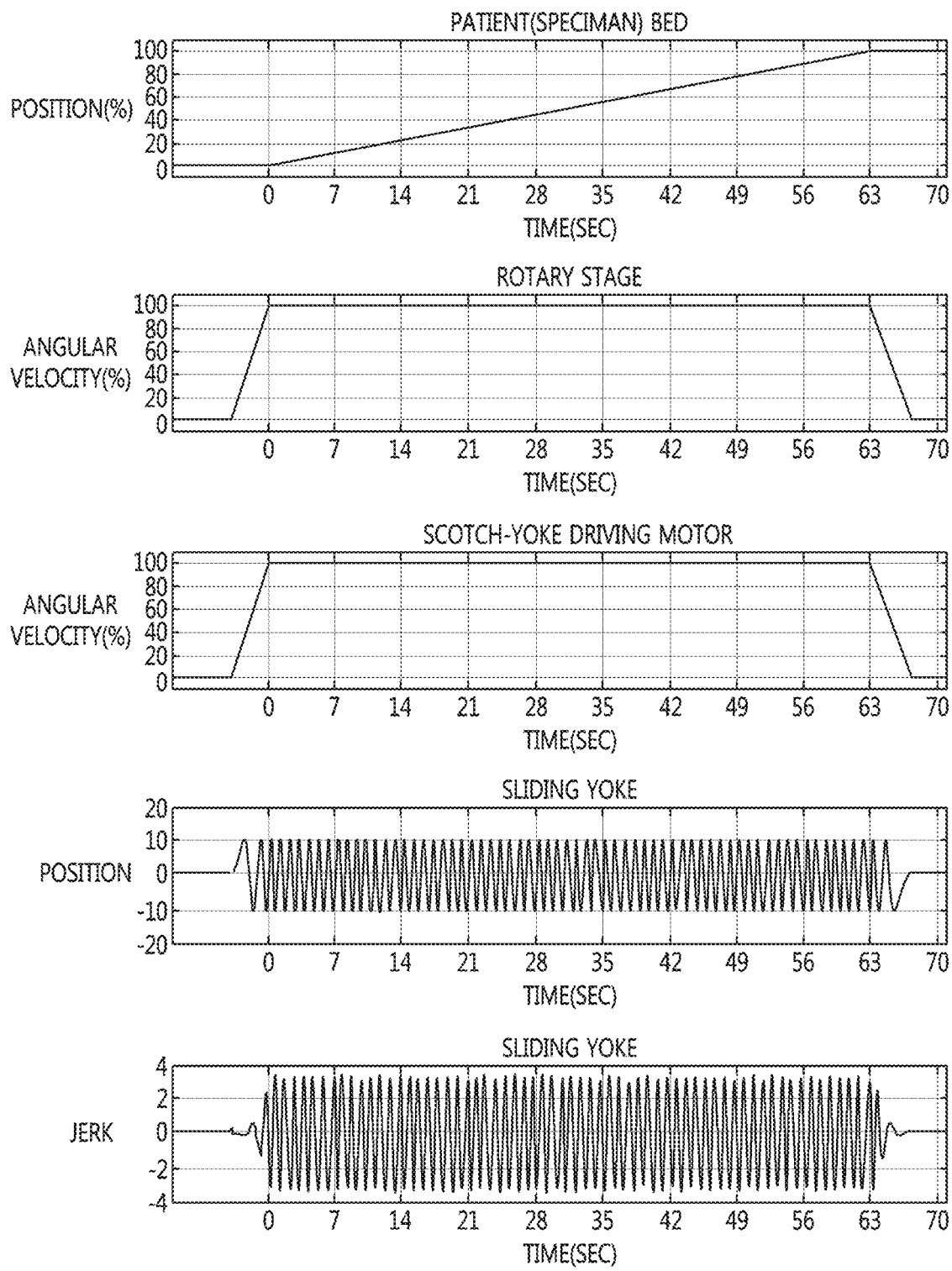
FIG. 27 and FIG. 28 are views for explaining 3D image generation according to an embodiment of the present invention.
Figure 28:
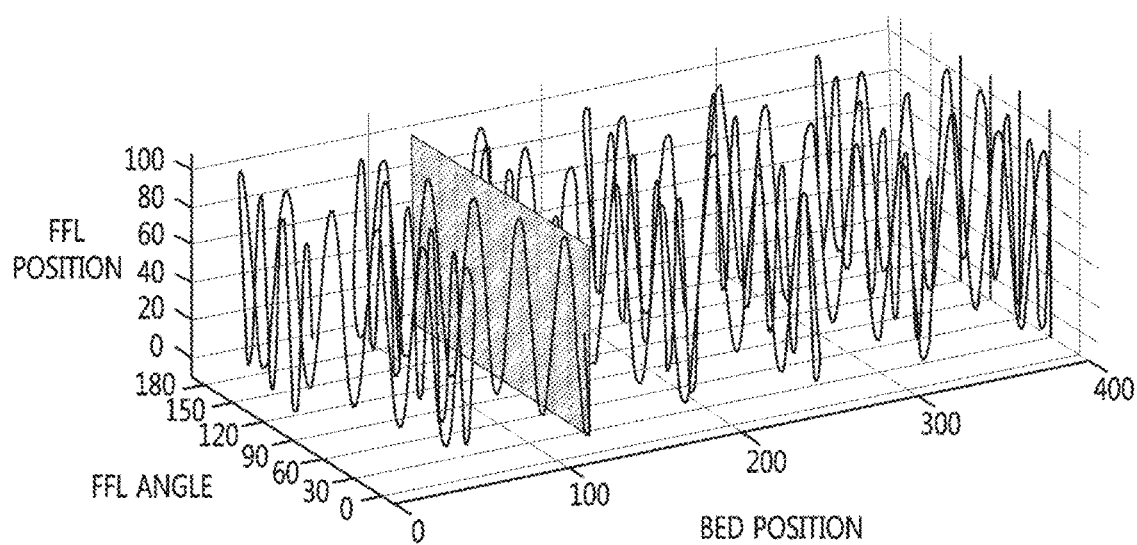

FIG. 27 and FIG. 28 are views for explaining 2D image generation according to a further embodiment of the present invention.

Referring to FIG. 27, according to a further embodiment, the control unit 130 may continuously linearly move the sample bed 150 with a constant velocity at step S321 illustrated in FIG. 22.

Also, the control unit 130 may continuously rotate the gradient magnetic field generation unit 120 rapidly at step S322 illustrated in FIG. 22.

To this end, the control unit 130 may adjust the angular velocity of the second motor 221d of the scotch yoke 221 at steps S323 and S324. That is, when the rotation part 212 is continuously rotated rapidly, the control unit 130 may increase the angular velocity of the second motor 221d such that the sliding yoke reciprocates with a sinusoidal motion a predetermined number of times while the rotation part 212 is continuously rotated.

Referring to FIG. 28, the rotation angle θ(t) of the FFL is continuously increased from 0 degrees, which is a reference angle. Here, when the rotation angle is limited so as to fall within a range from 0 degrees to 180 degrees using $\cos^{-1} \cos(\theta(t))$, the measured value I(t) may be arranged in the 3D space. Also, the 2D sinogram of the desired cross section may be generated through interpolation using adjacent points in the space, e.g., using up to eight adjacent points.

According to an embodiment, because problems related to a large amount of power and overheating of a coil are alleviated, it is advantageous in increasing the size of an apparatus applicable to a human body and to commercialize the apparatus.

According to an embodiment, compared to the case in which a gradient magnetic field generation unit is driven using a linear stage, little vibration is caused in a system, and fast reciprocating motion of an FFL is enabled, whereby the time taken to measure the cross section of a sample may be reduced.

Although embodiments of the present invention have been described with reference to the accompanying drawings, those skilled in the art will appreciate that the present invention may be practiced in other specific forms without changing the technical spirit or essential features of the present invention. Therefore, the embodiments described above are illustrative in all aspects and should not be understood as limiting the present invention.

What is claimed is:

1. An apparatus for imaging nano magnetic particles, comprising:
   a measurement head in which an excitation coil and a detection coil are installed and in which a sample bed, on which a sample including nano magnetic particles is placed, is accommodated;
   a gradient magnetic field generation unit for generating a magnetic field having a strength equal to or greater than a strength of a saturation magnetic field of the nano magnetic particles in a spacing area between identical magnetic poles facing each other and for forming a field-free region, in which there is a weak magnetic field or no magnetic field, in a portion of the spacing area;
   a first driving unit for linearly moving the sample bed in a direction in the spacing area;
   a second driving unit for rotating the gradient magnetic field generation unit in a plane perpendicular to the direction;
   a third driving unit that converts rotation into sinusoidal reciprocation by causing the gradient magnetic field generation unit to linearly reciprocate in the plane; and
   a control unit for applying a signal to the excitation coil when the sample bed is located in the spacing area of the gradient magnetic field generation unit, controlling the first driving unit, the second driving unit, and the third driving unit so as to move the field-free region in the sample, and imaging a 3D positional distribution of the nano magnetic particles included in the sample based on a detection signal output from the detection coil.

2. The apparatus of claim 1, wherein the excitation coil includes a low-frequency coil and a high-frequency coil and generates a mixed magnetic field by mixing a first magnetic field, generated in the low-frequency coil, with a second magnetic field, generated in the high-frequency coil.

3. The apparatus of claim 1, wherein the identical magnetic poles facing each other are formed using a pair of permanent magnets that generate a gradient magnetic field in the plane.

4. The apparatus of claim 3, wherein the identical magnetic poles facing each other are further formed using a pair of DC coils that generate a gradient magnetic field in another plane perpendicular to the plane.

5. The apparatus of claim 1, wherein the second driving unit comprises:
   a support in which a through hole is formed;
   a rotation part formed in a cylindrical shape to be inserted into the through hole, the rotation part accommodating the gradient magnetic field generation unit by joining the gradient magnetic field generation unit to an inner side thereof; and
   a first motor for rotating the rotation part in response to a control signal input from the control unit.

6. The apparatus of claim 5, further comprising: a first detection unit for measuring a reference point or a rotation angle of the rotation part.

7. The apparatus of claim 5, wherein: the rotation part further comprises a linear guide joined to the gradient magnetic field generation unit on the inner side thereof, the linear guide guiding the gradient magnetic field generation unit so as to linearly move in the plane, and the third driving unit is a scotch yoke that is formed to be joined between the inner side of the rotation part and the gradient magnetic field generation unit, the scotch yoke causing the gradient magnetic field generation unit to linearly reciprocate along the linear guide by converting rotation into sinusoidal reciprocation.

8. The apparatus of claim 7, wherein the scotch yoke comprises:
   a sliding yoke fixed to the gradient magnetic field generation unit and including a slot formed in a direction perpendicular to a transfer direction of the linear guide;
   a crank to which an eccentric pin engaging the slot is joined as an integral part thereof; and
   a second motor supplying torque to a center of the crank.

9. The apparatus of claim 8, wherein a mass of the crank is equivalent to a mass of the gradient magnetic field generation unit.

10. The apparatus of claim 8, wherein the crank is used as a flywheel having an increased moment of rotational inertia.

11. The apparatus of claim 8, further comprising: a second detection unit for measuring a reference point or a rotation angle of a central axis of the crank.

12. The apparatus of claim 8, wherein the control unit is configured to: generate a 2D image, which is a 2D positional distribution of nano magnetic particles included in a cross section of the sample, based on the detection signal, and generate a 3D image by synthesizing multiple 2D images corresponding to multiple cross sections that are parallel to each other.

13. The apparatus of claim 12, wherein the control unit is configured to: perform control so as to repeat rotation of the gradient magnetic field generation unit by the second driving unit and linear reciprocation thereof by the third driving unit, and generate a sinogram using a signal output from the detection signal according to movement of the field-free region and generate the 2D image by performing inverse radon transform on the generated sinogram.

14. The apparatus of claim 13, wherein the control unit is configured to: control the second driving unit so to intermittently rotate the gradient magnetic field generation unit, and delete data acquired during rotation from a sinogram generated as a result of intermittent rotation.

15. The apparatus of claim 13, wherein the control unit is configured to: control the second driving unit to continuously rotate the gradient magnetic field generation unit, and generate a sinogram through 2D interpolation of a detection signal acquired as a result of continuous rotation.

16. A method for imaging nano magnetic particles, comprising:
applying a signal to an excitation coil installed in a measurement head in which a sample including nano magnetic particles is accommodated; and
generating a magnetic field having a strength equal to or greater than a strength of a saturation magnetic field of the nano magnetic particles in a spacing area between identical magnetic poles facing each other, moving a field-free region, in which there is a weak magnetic field or no magnetic field and which is formed in a portion of the spacing area, in the sample, and imaging a 3D positional distribution of the nano magnetic particles included in the sample based on a detection signal output from a detection coil of the measurement head,
wherein the field-free region is linearly moved in a direction, is rotated in a plane perpendicular to the direction, and linearly reciprocates in the plane through conversion of rotation into sinusoidal reciprocation.

17. The method of claim 16, wherein imaging the 3D positional distribution comprises:
generating a 2D image, which is a 2D positional distribution of nano magnetic particles included in a cross section of the sample, based on the detection signal; and
generating a 3D image by synthesizing multiple 2D images corresponding to multiple cross sections that are parallel to each other.

18. The method of claim 17, wherein generating the 2D image comprises:
repeating rotation and linear reciprocation of the field-free region;
generating a sinogram using a signal output from the detection signal according to movement of the field-free region; and
generating the 2D image by performing inverse radon transform on the generated sinogram.

19. The method of claim 18, wherein generating the 2D image is configured to intermittently rotate the field-free region and to delete data acquired during rotation from the sinogram generated as a result of intermittent rotation.

20. The method of claim 18, wherein generating the 2D image is configured to continuously rotate the field-free region and to generate the sinogram through 2D interpolation of the detection signal acquired as a result of continuous rotation.

* * * * *